United States Patent [19]
Harada et al.

[11] Patent Number: 5,529,977
[45] Date of Patent: Jun. 25, 1996

[54] TRIAZINE DERIVATIVE, PROCESS FOR PREPARING THE SAME AND HERBICIDE USING THE SAME

[75] Inventors: Katsumasa Harada; Takaaki Abe; Yuji Akiyoshi; Akio Matsushita; Mikio Kojima; Ikuo Shiraishi; Kaoru Yamamoto; Takashi Hayama, all of Ube, Japan

[73] Assignee: UBE Industries, Ltd., Yamaguchi-ken, Japan

[21] Appl. No.: 326,830

[22] Filed: Oct. 21, 1994

Related U.S. Application Data

[62] Division of Ser. No. 894,557, Jun. 5, 1992, Pat. No. 5,387,575.

[30] Foreign Application Priority Data

| Jun. 7, 1991 | [JP] | Japan | 3-232594 |
| Jun. 7, 1991 | [JP] | Japan | 3-232595 |
| Jun. 7, 1991 | [JP] | Japan | 3-232596 |
| Jun. 25, 1991 | [JP] | Japan | 3-248533 |

[51] Int. Cl.⁶ .............. C07D 251/34; C07D 251/16; C07D 403/12; A01N 43/66

[52] U.S. Cl. .............. 504/227; 544/219; 504/230

[58] Field of Search .............. 544/219; 504/230, 504/227

[56] References Cited

U.S. PATENT DOCUMENTS

| 4,968,340 | 11/1990 | Kaku et al. | 544/317 |
| 5,238,934 | 8/1993 | Knuppel et al. | 514/241 |
| 5,317,005 | 5/1994 | Jones | 504/239 |
| 5,376,620 | 12/1994 | Abe et al. | 504/243 |

FOREIGN PATENT DOCUMENTS

| 59096 | 1/1991 | Australia. |
| 347811 | 12/1989 | European Pat. Off.. |
| 409369 | 1/1991 | European Pat. Off.. |
| 411706 | 2/1991 | European Pat. Off.. |
| 135963 | 3/1990 | Japan. |
| 85262 | 3/1990 | Japan. |
| 66672 | 3/1991 | Japan. |
| 200772 | 9/1991 | Japan. |

OTHER PUBLICATIONS

Borch, R. F., "A New Procedure for the Darzens Synthesis of Glycidic Esters", Tetrahedron Letters 36:3761–3763 (1972).

Degner et al, Chemical Abstracts, vol. 115, entry 29369 (1991).

*Primary Examiner*—John M. Ford
*Attorney, Agent, or Firm*—Finnegan, Henderson, Farabow, Garrett & Dunner

[57] ABSTRACT

Disclosed are a pyrimidine or triazine compound represented by the following formula (I):

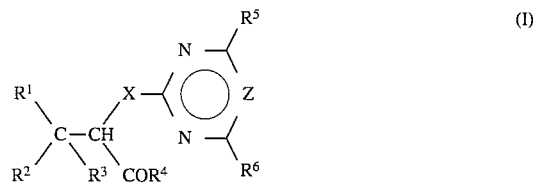

wherein $R^1$ represents cyano group, a halogen atom, hydroxy group or $-O-R^7$ where $R^7$ represents a lower alkyl group, a lower alkenyl group, a lower alkynyl group, a halo-lower alkyl group or a cyano-lower alkyl group; $R^2$ represents hydrogen atom or a lower alkyl group; $R^3$ represents hydrogen atom or a lower alkyl group; $R^4$ represents a 1-imidazolyl group, $-NHSO_2-R^8$ where $R^8$ represents a lower alkyl group or a phenyl group which may have a substituent, hydroxy group, a lower alkoxy group or a benzyloxy group when Z is nitrogen atom; or a 1-imidazolyl group, $-NHSO_2-R^8$ where $R^8$ has the same meaning as defined above, hydroxy group, OK, a lower alkoxy group which may have a substituent, a lower alkenyloxy group, a lower alkynyloxy group, a cycloalkoxy group which may have a substituent, a phenoxy group, a benzyloxy group, a lower alkylthio group, a phenylthio group or an alkylsulfonylamino group when Z is $-CH=$ group; $R^5$ represents a lower alkoxy group; $R^6$ represents a lower alkoxy group or a lower alkyl group; X represents oxygen atom or sulfur atom; and Z represents nitrogen atom or $-CH=$ group.

processes for preparing the same and a herbicide containing the same as an active ingredient(s).

9 Claims, No Drawings

TRIAZINE DERIVATIVE, PROCESS FOR PREPARING THE SAME AND HERBICIDE USING THE SAME

This is a division of application Ser. No. 07/894,557, filed Jun. 5, 1992, now U.S. Pat. No. 5,387,575.

BACKGROUND OF THE INVENTION

This invention relates to a herbicide containing a novel pyrimidine or triazine derivative such as 3-alkoxybutyrylimidazole derivatives, 3-alkoxyalkanoic acid amide derivatives, 3-alkoxyalkanoic acid derivatives and 2-pyrimidinylthioalkanoic acid derivatives as an active ingredient.

Many herbicides have heretofore been developed for promoting labor-saving of farm practices and increase in productivity of crops. Conventional herbicides are, however, not sufficient in herbicidal effect, e.g. insufficient in selective herbicidal effect to crops such as cotton, and also not sufficiently satisfactory in the point of safety to creatures. Thus, in order to solve these problems, development of a novel herbicide has been demanded.

3-Alkoxybutyrylimidazole derivatives, 3-alkoxyalkanoic acid amide derivatives and 3-alkoxyalkanoic acid derivatives of the present invention are novel compounds and their herbicidal effect have not yet been known.

As a compound similar to the 2-pyrimidinylthioalkanoic acid derivative of the present invention, there has been known, for example, compounds disclosed in Japanese Provisional Patent Publication No. 85262/1990, and it has been also known that these compounds have herbicidal activities. However, herbicidal effects of these compounds are insufficient, and thus, it has been desired to develop a novel herbicide having more excellent activities.

SUMMARY OF THE INVENTION

An object of the present invention is to provide a novel pyrimidine or triazine derivative, a process for preparing the same and a herbicide containing said compound as an active ingredient.

The present inventors have studied intensively in order to solve the above problems, and consequently found that a novel pyrimidine or triazine derivative shows more excellent herbicidal effect against annual rice plant weeds and annual broad-leaved weeds and shows selectivity to crops such as cotton, and also found a process for preparing the same with high yields, to accomplish the present invention.

The present invention is described below.

That is, the first invention is concerned to a 3-alkoxyalkanoic acid derivative represented by the following formula (I):

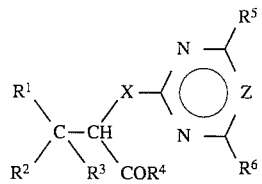

wherein $R^1$ represents cyano group, a halogen atom, hydroxy group or —O—$R^7$ where $R^7$ represents a lower alkyl group, a lower alkenyl group, a lower alkynyl group, a halo-lower alkyl group or a cyano-lower alkyl group; $R^2$ represents hydrogen atom or a lower alkyl group; $R^3$ represents hydrogen atom or a lower alkyl group; $R^4$ represents a 1-imidazolyl group, —NHSO$_2$—$R^8$ where $R^8$ represents a lower alkyl group or a phenyl group which may have a substituent, hydroxy group, a lower alkoxy group or a benzyloxy group when Z is nitrogen atom; or a 1-imidazolyl group, —NHSO$_2$—$R^8$ where $R^8$ has the same meaning as defined above, hydroxy group, OK, a lower alkoxy group which may have a substituent, a lower alkenyloxy group, a lower alkynyloxy group, a cycloalkoxy group which may have a substituent, a phenoxy group, a benzyloxy group, a lower alkylthio group, a phenylthio group or an alkylsulfonylamino group when Z is —CH= group; $R^5$ represents a lower alkoxy group; $R^6$ represents a lower alkoxy group or a lower alkyl group; X represents oxygen atom or sulfur atom; and Z represents nitrogen atom or —CH= group.

The second invention is concerned to a 3-alkoxybutyrylimidazole derivative represented by the following formula (Ia):

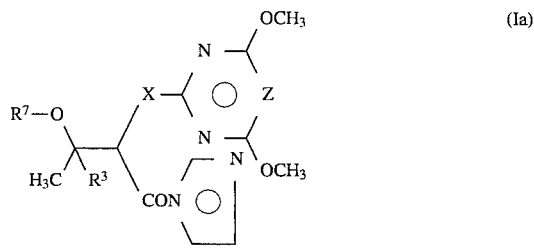

wherein $R^7$, $R^3$, X and Z each have the same meanings as defined above.

The third invention is concerned to a 3-alkoxyalkanoic acid amide derivative represented by the following formula (Ib):

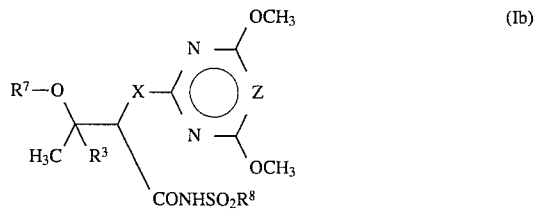

wherein $R^7$, $R^3$, $R^8$, X and Z each have the same meanings as defined above.

The fourth invention is concerned to a triazine derivative represented by the following formula (Ic):

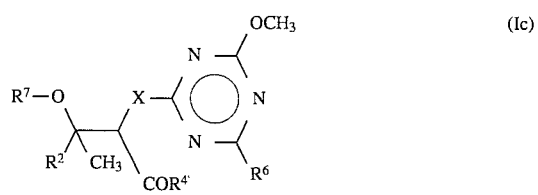

wherein $R^{4'}$ represents hydroxy group, a lower alkoxy group or a benzyloxy group; $R^2$, $R^6$, $R^7$ and X each have the same meanings as defined above.

The fifth invention is concerned to a 2-pyrimidinylthioalkanoic acid derivative represented by the following formula (Id):

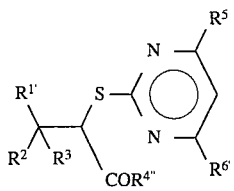

(Id)

wherein $R^{1'}$ represents cyano group or a halogen atom; $R^2$ represents a lower alkyl group; $R^{4''}$ represents hydroxy group, OK, a lower alkoxy group which may have a substituent, a lower alkenyloxy group, a lower alkynyloxy group, a cycloalkoxy group which may have a substituent, a phenoxy group, a benzyloxy group, a lower alkylthio group, a phenylthio group, a 1-imidazolyl group or —NHSO$_2$—R$^8$ where $R^8$ has the same meaning as defined above; $R^{6'}$ represents a lower alkoxy group; $R^3$ and $R^5$ each have the same meanings as defined above.

The sixth invention is concerned to a 3-hydroxy-2-pyrimidinylthioalkanoic acid derivative represented by the following formula (Ie):

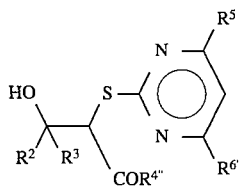

(Ie)

wherein $R^2$, $R^3$, $R^{4''}$, $R^5$ and $R^{6'}$ each have the same meanings as defined above.

The seventh invention is concerned to a process for preparing the 3-alkoxyalkanoic acid derivative represented by the above formula (Ia), which comprises reacting a compound represented by the following formula (II):

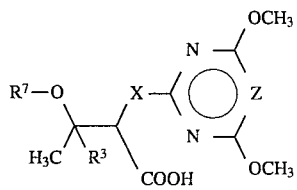

(II)

wherein $R^7$, $R^3$, X and Z each have the same meanings as defined above, with N,N'-carbonyldiimidazole.

The eighth invention is concerned to a process for preparing the 3-alkoxyalkanoic acid amide derivative represented by the above formula (Ib), which comprises reacting the 3-alkoxyalkanoic acid derivative represented by the above formula (Ia) with a compound represented by the following formula (III):

NH$_2$SO$_2$R$^8$     (III)

wherein $R^8$ has the same meaning as defined above.

The ninth invention is concerned to a process for preparing the triazole derivative represented by the above formula (Ic), which comprises reacting a compound represented by the following formula (IV):

(IV)

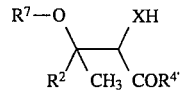

wherein $R^2$, $R^{4'}$, $R^7$ and X each have the same meanings as defined above, with a compound represented by the following formula (V):

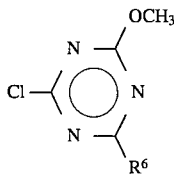

(V)

wherein $R^6$ has the same meaning as defined above.

The tenth invention is concerned to a process for preparing the imidazole derivative represented by the above formula (Ic), which comprises reacting a compound represented by the following formula (IV):

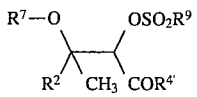

(VI)

wherein $R^2$, $R^{4'}$ and $R^7$ each have the same meanings as defined above, and $R^9$ represents a lower alkyl group, a substituted phenyl group or a halo-lower alkyl group, with a compound represented by the following formula (V):

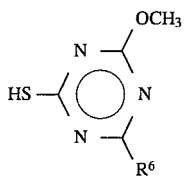

(VII)

wherein $R^6$ has the same meaning as defined above.

The eleventh invention is concerned to a process for preparing the triazole derivative represented by the above formula (Ic), which comprises subjecting to interesterification of a compound represented by the following formula (VIII):

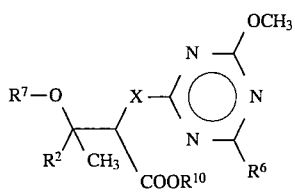

(VIII)

wherein $R^2$, $R^6$, $R^7$ and X each have the same meanings as defined above, and $R^{10}$ represents a lower alkyl group.

The twelfth invention is concerned to a process for preparing the triazole derivative represented by the above formula (Ic), which comprises subjecting to hydrogenolysis of a compound represented by the following formula (IX):

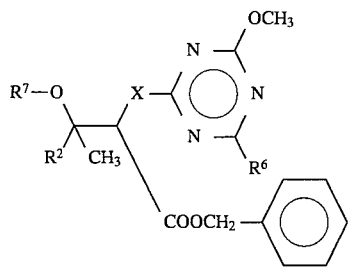

(IX)

wherein $R^2$, $R^6$, $R^7$ and X each have the same meanings as defined above.

The thirteenth invention is concerned to a process for preparing a 3-halogeno-2-pyrimidinylthioalkanoic acid derivative represented by the following formula (Id'):

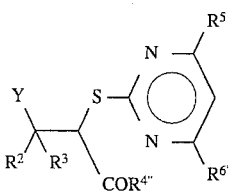

wherein Y represents a halogen atom; $R^2$, $R^3$, $R^{4''}$, $R^5$ and $R^{6'}$ each have the same meanings as defined above,
which comprises reacting the 3-hydroxy-2-pyrimidinylthioalkanoic acid derivative represented by the above formula (Ie) with a halogenating agent.

The fourteenth invention is concerned to a process for preparing a 3-cyano-2-pyrimidinylthioalkanoic acid derivative represented by the following formula (Id''):

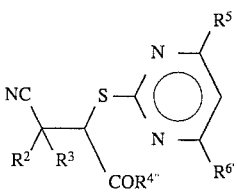

wherein $R^2$, $R^3$, $R^{4''}$, $R^5$ and $R^{6'}$ each have the same meanings as defined above, which comprises reacting the 3-halogeno-2-pyrimidinylthioalkanoic acid derivative represented by the above formula (Id') with a cyanizing agent.

The fifteenth invention is concerned to a process for preparing the 3-hydroxy-2-pyrimidinylthioalkanoic acid derivative represented by the above formula (Ie) which comprises reacting a compound represented by the formula (X):

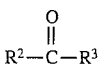

wherein $R^2$ and $R^3$ each have the same meanings as defined above, with a compound represented by the following formula (XI):

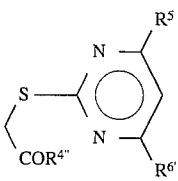

wherein $R^{4''}$, $R^5$ and $R^{6'}$ each have the same meanings as defined above.

The sixteenth invention is concerned to a herbicide comprising the pyrimidine or triazine derivative represented by the above formula (I) as an active ingredient.

DESCRIPTION OF THE PREFERRED EMBODIMENTS

In the following, the present invention is explained in detail.

In the novel pyrimidine or triazine derivative (I) including the compounds of the formulae (Ia) to (Ie) which are the desired compounds of the present invention and the compounds (II) to (VII) which are starting materials thereof, $R^1$, $R^{1'}$, $R^2$, $R^3$, $R^4$, $R^{4'}$, $R^{4''}$, $R^5$, $R^6$, $R^{6'}$, $R^7$, $R^8$, X, Y and Z are as described below.

As $R^1$, there may be mentioned cyano group, a halogen atom (fluorine atom, chlorine atom, bromine atom and iodine atom), hydroxy group, or —O—$R^7$. As $R^7$ there may be mentioned a lower alkyl group, a lower alkenyl group, a lower alkynyl group, a halo-lower alkyl group and a cyano-lower alkyl group, and as a lower alkyl group, preferably a straight or branched alkyl group having 1 to 6 carbon atoms, more preferably those having 1 to 4 carbon atoms, particularly preferably those having 1 to 3 carbon atoms (e.g. methyl group, ethyl group, n-propyl group and i-propyl group); as a lower alkenyl group, preferably a straight or branched alkenyl group having 2 to 6 carbon atoms, more preferably those having 2 to 5 carbon atoms, particularly preferably those having 2 to 3 carbon atoms (e.g. propenyl group); as a lower alkynyl group, preferably a straight or branched alkynyl group having 2 to 6 carbon atoms, more preferably those having 2 to 5 carbon atoms, particularly preferably those having 2 to 3 carbon atoms (e.g. propynyl group); as a halo-lower alkyl group, preferably a straight or branched haloalkyl group having 1 to 6 carbon atoms (as the halogen atom, there may be mentioned fluorine atom, chlorine atom, bromine atom and iodine atom, but chlorine atom is more preferred), more preferably those having 1 to 5 carbon atoms, particularly preferably those having 1 to 3 carbon atoms (e.g. chloroethyl group and chloropropyl group); and as a cyano-lower alkyl group, preferably a straight or branched cyanoalkyl group having 1 to 6 carbon atoms, more preferably those having 1 to 5 carbon atoms, particularly preferably those having 1 to 3 carbon atoms (e.g. cyanoethyl group).

As $R^2$, there may be mentioned a lower alkyl group, and the lower alkyl group is preferably a straight or branched alkyl group having 1 to 6 carbon atoms; more preferably those having 1 to 4 carbon atoms, particularly preferably those having 1 to 3 carbon atoms (e.g. methyl group, ethyl group, n-propyl group and i-propyl group) and methyl group is most preferred.

As $R^3$, there may be mentioned hydrogen atom and a lower alkyl group, and the lower alkyl group is preferably a straight or branched alkyl group having 1 to 6 carbon atoms; more preferably those having 1 to 4 carbon atoms, particularly preferably those having 1 to 3 carbon atoms (e.g. methyl group and ethyl group).

When Z represents nitrogen atom, as $R^4$, there may be mentioned a 1-imidazolyl group as in the formula (Ia), —NHSO$_2$—$R^8$ (an alkylsulfonylamino group or an arylsulfonylamino group) where $R^8$ represents a lower alkyl group or a phenyl group which may have a substituent as in the formula (Ib), hydroxy group, a lower alkoxy group or a benzyloxy group as in the formula (Ic). The lower alkyl group of $R^8$ is preferably a straight or branched alkyl group having 1 to 6 carbon atoms; more preferably those having 1 to 4 carbon atoms (e.g. methyl group, ethyl group, n-propyl group, isopropyl group and n-butyl group). As the substituent for the phenyl group of $R^8$, there may be mentioned, for example, a straight or branched alkyl group having 1 to 6 carbon atoms (more preferably those having 1 to 4 carbon atoms, most preferably methyl group) and a halogen atom (fluorine atom, chlorine atom, bromine atom and iodine atom, preferably chlorine atom). The lower alkoxy group is preferably a straight or branched alkoxy group having 1 to 6 carbon atoms, more preferably those having 1 to 4 carbon atoms, particularly preferably those having 1 to 3 carbon atoms (e.g. methoxy group and ethoxy group).

When Z represents —CH=, as $R^4$, there may be mentioned a 1-imidazolyl group as in the formula (Ia), —NHSO$_2$—$R^8$ as in the formula (Ib), hydroxy group, OK, a lower alkoxy group which may have a substituent, a lower alkenyloxy group, a lower alkynyloxy group, a cycloalkoxy group which may have a substituent, a phenoxy group, a benzyloxy group, a lower alkylthio group, a phenylthio group or an alkylsulfinylamino group as in the formulae (Id) and (Ie). Here, $R^8$ is the same as mentioned above. As the carbon number in the lower alkoxy group, lower alkylthio group and alkylsulfonylamino group, preferably a straight or branched one having 1 to 6, more preferably 1 to 4, particularly preferably 1 to 3 carbon atoms; as the substituent for the lower alkoxy group, there may be mentioned a straight or branched lower alkoxy group having 1 to 6 (preferably 1 to 4, more preferably 1 to 3) carbon atoms and a lower alkylsilyl group (e.g. trimethylsilyl group); as the lower alkenyl group, preferably a straight or branched one having 2 to 6, more preferably 2 to 4, particularly preferably 2 to 3 carbon atoms (e.g. propenyl group); as the lower alkynyl group, preferably a straight or branched one having 2 to 6, more preferably 2 to 4, particularly preferably 2 to 3 carbon atoms (e.g. propynyl group); as the cycloalkoxy group, preferably those having 3 to 10, more preferably 3 to 8, particularly preferably 4 to 6 carbon atoms; and as the substituent for the cycloalkoxy group, there may be mentioned a halogen atom, preferably chlorine atom.

As $R^5$, there may be mentioned methoxy group as in the formulae (Ia) to (Ic), or a straight or branched lower alkoxy group having 1 to 6 carbon atoms, and the number of the carbon atoms in the lower alkoxy group is preferably 1 to 4, more preferably 1 to 3 (e.g. methoxy group).

As $R^6$, there may be mentioned methoxy group as in the formulae (Ia) and (Ib), or a lower alkyl group or a lower alkoxy group as in the formulae (Ic) to (Ie). As the lower alkyl group, there may be mentioned a straight or branched alkyl group having 1 to 6, more preferably 1 to 4, particularly preferably 1 to 3 carbon atoms (e.g. methyl and ethyl group), and the lower alkoxy group is preferably a straight or branched alkoxy group having 1 to 6, more preferably 1 to 4, particularly preferably 1 to 3 carbon atoms (e.g. methoxy group and ethoxy group).

As $R^9$ in the formula (VI), there may be mentioned a lower alkyl group, a substituted phenyl group and a halo-lower alkyl group, and as the lower alkyl group of the lower alkyl group and the halo-lower alkyl group, preferred are straight or branched one having 1 to 6 carbon atoms, more preferably 1 to 4 carbon atoms, particularly preferably 1 to 3 carbon atoms (e.g. methyl group and ethyl group); and as the substituent of the substituted phenyl group, there may be mentioned a straight or branched alkyl group having 1 to 6, preferably 1 to 4, more preferably 1 to 3 carbon atoms.

As $R^{10}$ in the formula (VIII), there may be mentioned a lower alkyl group, and preferably a straight or branched one having 1 to 6 carbon atoms, more preferably 1 to 4 carbon atoms, particularly preferably 1 to 3 carbon atoms (e.g. methyl group and ethyl group).

As X, there may be mentioned oxygen atom and sulfur atom.

As Z, there may be mentioned nitrogen atom and —CH= (methyn group).

As Y in the formula (Id), there may be mentioned a halogen atom (e.g. fluorine atom, chlorine atom, bromine atom and iodine atom, but preferably chlorine atom).

The novel pyrimidine or triazine derivative (I) which is a desired compound may include an optical isomer based on an asymmetric carbon atom.

The compound (I) can be prepared by, for example, Preparation method 1 to Preparation method 11 shown below.

PREPARATION METHOD 1

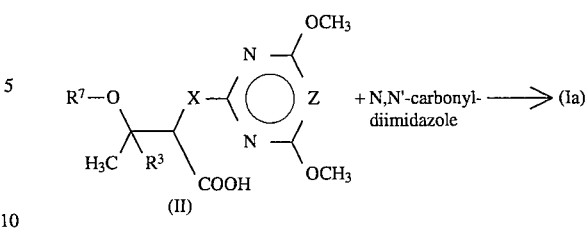

wherein $R^3$, $R^7$, X and Z each have the same meanings as defined above.

The compound (Ia) can be prepared by reacting the starting compound (II) with N,N'-carbonyldiimidazole in a solvent.

The compound (II) can be prepared easily by, for example, reacting 2-hydroxyalkanoic acid derivative or 2-mercaptoalkanoic acid derivative with a 2-methylsulfonylpyridine or a 2-chlorotriazine according to the method described in Japanese Patent Application No. 270320/1990 as shown below.

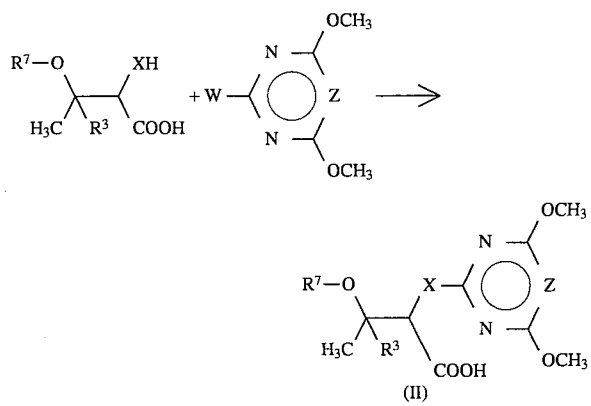

wherein $R^3$, $R^7$, X and Z each have the same meanings as defined above, and W represents chlorine atom or $CH_3SO_2$—.

As the compound (II), there may be mentioned, for example, the respective compounds (referred to as Compounds (II)1 to (II)38) comprising the respective kinds of substituted groups corresponding to Compounds No. 1 to No. 38 shown in Table 1 (for example, the compound (II) corresponding to Compound No. 1 is referred to as Compound $(II)_1$, and this Compound $(II)_1$ means a compound wherein $R^7$ is $CH_3$, $R^3$ is H, X is O and Z is CH in the compound (II)).

The solvent is not particularly limited so long as it does not participate in the present reaction directly, and may include, for example, water; ethers such as diethyl ether, tetrahydrofuran and 1,4-dioxane; ketones such as acetone, methyl ethyl ketone and methyl isobutyl ketone; nitriles such as acetonitrile; bipolar aprotic solvents such as N,N-dimethylformamide, N,N'-dimethyl-2-imidazolidinone and dimethyl sulfoxide; halogenated alkyl solvents such as chloroform and methylene chloride; and a mixture of the above solvents.

The reaction for preparing the compound (Ia) can be carried out at a reaction concentration of 5 to 80%.

In the preparation method, the ratio of using the starting compound (II) and N,N'-carbonyldiimidazole is that 0.5 to 2 mole, preferably 1 to 1.5 mole of N,N'-carbonyldiimidazole per mole of the starting compound (II).

The reaction temperature is not particularly limited so long as it is a boiling point of a solvent to be used or lower, but the reaction can be carried out generally at 0° to 80° C., preferably 5° to 50° C.

The reaction time varies depending on the above concentration and temperature, but may be generally carried out within 0.5 to 10 hours.

As the compound (Ia), there may be mentioned, for example, the respective compounds (referred to as Compounds 1 to 38) comprising the respective kinds of substituted groups corresponding to Compounds No. 1 to No. 38 shown in Table 1 (for example, the compound (I) corresponding to Compound No. 1 is referred to as Compound 1, and this Compound 1 means a compound wherein $R^7$ is $CH_3$, $R^3$ is H, X is O and Z is CH in the compound (I)).

PREPARATION METHOD 2

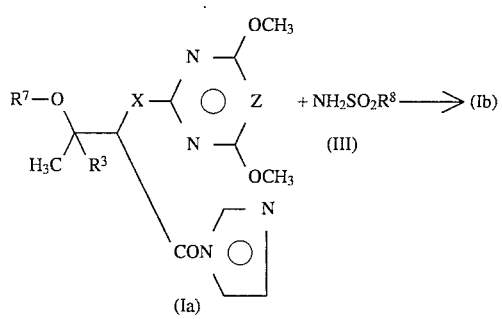

wherein $R^3$, $R^7$, $R^8$, X and Z each have the same meanings as defined above.

The compound (Ib) can be prepared by reacting the compound (Ia) with an alkylsulfonylamine or an arylsulfonyl amine represented by the formula (III) in a solvent in the presence of a base.

The compound of the formula (III) can be easily prepared by reacting a corresponding sulfonyl chloride and ammonia. As the compound (III), there may be mentioned, for example, the respective compounds (referred to as Compounds $(III)_{39}$ to $(III)_{140}$) comprising the respective kinds of substituted groups corresponding to Compounds No. 39 to No. 140 shown in Table 1, (for example, the compound (III) corresponding to Compound No. 41 is referred to as Compound $(III)_{41}$, and this Compound $(III)_{41}$ means a compound wherein $R^8$ is $CH_3$ in the compound (III)).

The solvent is not particularly limited so long as it does not participate in the present reaction directly, and may include, for example, ethers such as diethyl ether, tetrahydrofuran and 1,4-dioxane; ketones such as acetone, methyl ethyl ketone and methyl isobutyl ketone; nitriles such as acetonitrile; bipolar aprotic solvents such as N,N-dimethylformamide, N,N'-dimethyl-2-imidazolidinone and dimethyl sulfoxide; and a mixture of the above solvents.

As the base, there may be mentioned, for example, inorganic bases such as sodium amide, sodium hydroxide, potassium hydroxide, potassium carbonate, sodium carbonate and sodium hydride.

The reaction for preparing the compound (Ib) can be carried out at a reaction concentration of 5 to 80%.

In the preparation method, the ratio of using the starting compound (Ia) and the compound (III) is that 0.5 to 2 mole, preferably 1 to 1.5 mole of the compound (III) per mole of the starting compound (Ia).

The reaction temperature is not particularly limited so long as it is a boiling point of a solvent to be used or lower, but the reaction can be carried out generally at 0° to 50° C.

The reaction time varies depending on the above concentration and temperature, but may be generally carried out within 1 to 10 hours.

As the compound (Ib), there may be mentioned, for example, the respective compounds (referred to as Compounds 39 to 120) comprising the respective kinds of substituted groups corresponding to Compounds No. 39 to No. 140 shown in Table 1 (for example, the compound (I) corresponding to Compound No. 41 is referred to as Compound 41, and this Compound 41 means a compound wherein $R^7$ is $CH_3$, $R^3$ is H, $R^8$ is $CH_3$, X is S and Z is CH in the compound (I)).

PREPARATION METHOD 3

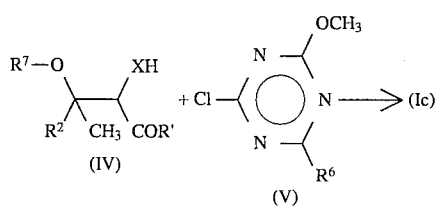

wherein $R^2$, $R^{4'}$, $R^6$, $R^7$ and X each have the same meanings as defined above.

The compound (Ic) can be generally prepared by reacting the starting compound (IV) and the starting compound (V) in a solvent in the presence of a base.

The compound (IV) wherein X is oxygen atom can be easily prepared, for example, by reacting epoxyalkanoates prepared according to the method described in "Tetrahedron Letter", No. 36, p. 3761 (1972) or "Org. Syn.", IV, p. 459 in an alcohol in the presence of an acid catalyst (sulfuric acid or paratoluenesulfonic acid) as shown below.

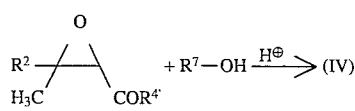

wherein $R^2$, $R^{4'}$ and $R^7$ each have the same meanings as defined above.

Also, the compound (IV) wherein X is sulfur atom can be easily prepared, for example, by reacting a compound (IV') with sodium hydrosulfite in a polar solvent as shown below.

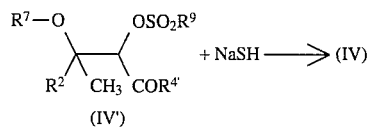

wherein $R^2$, $R^{4'}$, $R^7$ and $R^9$ each have the same meanings as defined above.

As the compound (IV), there may be mentioned, for example, the respective compounds comprising the respective kinds of substituted groups corresponding to Compounds Nos. 141, 144, 145, 148, 149, 150, 153, 154, 157, 158, 159, 162, 163, 164, 165, 167, 168, 169, 171, 172, 175, 176, 179 and 180 (which are referred to as Compounds $(IV)_{141}$, $(IV)_{144}$, $(IV)_{145}$, $(IV)_{148}$, $(IV)_{149}$, $(IV)_{150}$, $(IV)_{153}$, $(IV)_{154}$, $(IV)_{157}$, $(IV)_{158}$, $(IV)_{159}$, $(IV)_{162}$, $(IV)_{163}$, $(IV)_{164}$, $(IV)_{165}$, $(IV)_{167}$, $(IV)_{168}$, $(IV)_{169}$, $(IV)_{171}$, $(IV)_{172}$, $(IV)_{175}$, $(IV)_{176}$, $(IV)_{179}$ and $(IV)_{180}$, respectively) shown in Table 1 (for example, the compound (IV) corresponding to Compound No. 144 is referred to as Compound $(IV)_{144}$, and this Compound $(IV)_{144}$ means a compound wherein $R^7$ is $CH_3$, $R^2$ is H, $R^{4'}$ is OH and X is S in the compound (IV)).

The compound (V) wherein $R^6$ is an alkoxy group can be easily prepared, for example, by reacting a cyanuric acid and an alkylalcoholate as shown below.

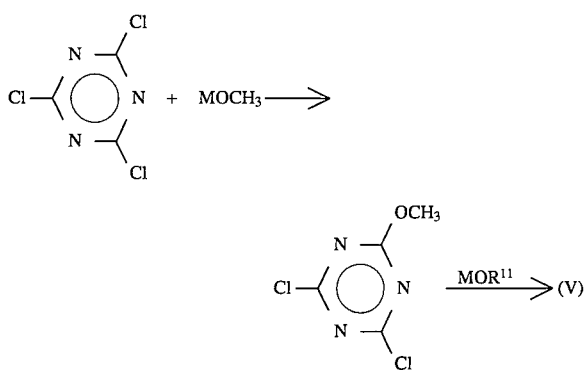

wherein $R^{11}$ represents an alkyl group and M represents an alkali metal.

The compound (V) wherein $R^6$ is an alkyl group can be easily prepared, for example, by reacting a cyanuric acid with a grignard reagent and further reacting sodium methoxide thereto as shown below.

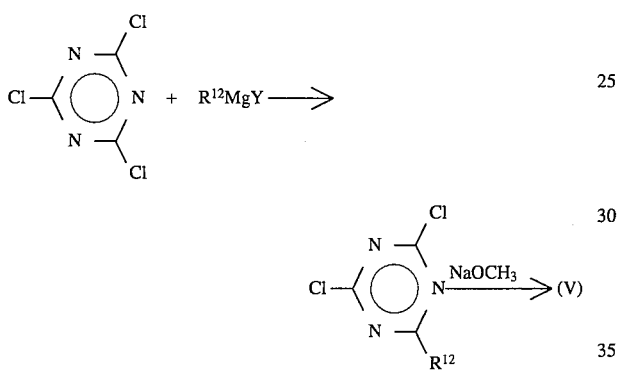

wherein $R^{12}$ represents an alkyl group and Y represents a halogen atom.

As the compound (V), there may be mentioned, for example, the respective compounds comprising the respective kinds of substituted groups corresponding to Compounds Nos. 141, 144, 145, 148, 149, 150, 153, 154, 157, 158, 159, 162, 163, 164, 165, 167, 168, 169, 171, 172, 175, 176, 179 and 180 (which are referred to as Compounds $(V)_{141}$, $(V)_{144}$, $(V)_{145}$, $(V)_{148}$, $(V)_{149}$, $(V)_{150}$, $(V)_{153}$, $(V)_{154}$, $(V)_{157}$, $(V)_{158}$, $(V)_{159}$, $(V)_{162}$, $(V)_{163}$, $(V)_{164}$, $(V)_{165}$, $(V)_{167}$, $(V)_{168}$, $(V)_{169}$, $(V)_{171}$, $(V)_{172}$, $(V)_{175}$, $(V)_{176}$, $(V)_{179}$ and $(V)_{180}$, respectively) shown in Table 1 (for example, the compound (V) corresponding to Compound No. 144 is referred to as Compound $(V)_{144}$, and this Compound $(V)_{144}$ means a compound wherein $R^6$ is $OCH_3$ in the compound (V)).

The solvent is not particularly limited so long as it does not participate in the present reaction directly, and may include, for example, water; ethers such as diethyl ether, tetrahydrofuran and 1,4-dioxane; ketones such as acetone, methyl ethyl ketone and methyl isobutyl ketone; nitriles such as acetonitrile; bipolar aprotic solvents such as N,N-dimethylformamide, N,N'-dimethyl-2-imidazolidinone and dimethyl sulfoxide; and a mixture of the above solvents.

As the base, there may be mentioned an organic base such as triethylamine, pyridine and N,N-diethylaniline; and an inorganic base such as sodium amide, sodium hydroxide, potassium hydroxide, potassium carbonate, sodium carbonate and sodium hydride.

The reaction for preparing the compound (Ic) can be carried out at a reaction concentration of 5 to 80%.

In the preparation method, the ratio of using the starting compounds (IV) and (V) is that 0.5 to 2 mole, preferably 1 to 1.5 mole of the starting compound (V) per mole of the starting compound (IV).

The reaction temperature is not particularly limited so long as it is a boiling point of a solvent to be used or lower, but the reaction can be carried out generally at 0° to 50° C., and the reaction time can be shortened by heating.

The reaction time varies depending on the above concentration and temperature, but may be generally carried out within 0.5 to 10 hours.

As the compound (Ic), there may be mentioned, for example, the respective compounds (referred to as Compounds 141 to 180) comprising the respective kinds of substituted groups corresponding to Compounds No. 141 to No. 180 shown in Table 1 (for example, the compound (I) corresponding to Compound No. 144 is referred to as Compound 144, and this Compound 144 means a compound wherein $R^7$ is $CH_3$, $R^2$ is H, $R^{4'}$ is OH, $R^6$ is $OCH_3$ and X is S in the compound (I)).

PREPARATION METHOD 4

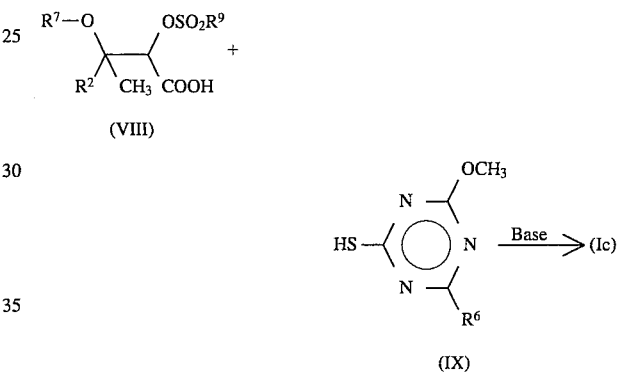

wherein $R^2$, $R^{4'}$, $R^6$, $R^7$ and $R^9$ each have the same meanings as defined above.

The compound (Ic) can be prepared by using a starting compound (VIII) in place of the compound (IV) in Preparation method 3 and using a starting compound (IX) in place of the compound (V) in the same and reacting them.

The compound (VIII) can be easily prepared, for example, by reacting the compound (IV) and sulfonyl chloride in a suitable solvent in the presence of a base catalyst as shown below.

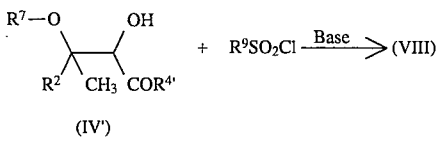

wherein $R^2$, $R^{4'}$, $R^7$ and $R^9$ each have the same meanings as defined above.

As the compound (VIII), there may be mentioned, for example, the respective compounds comprising the respective kinds of substituted groups corresponding to Compounds Nos. 144, 148, 153, 157, 158, 162, 164, 167, 168, 171, 175, 179 and 180 (which are referred to as Compounds $(VIII)_{144}$, $(VIII)_{148}$, $(VIII)_{153}$, $(VIII)_{157}$, $(VIII)_{158}$, $(VIII)_{162}$, $(VIII)_{164}$, $(VIII)_{167}$, $(VIII)_{168}$, $(VIII)_{171}$, $(VIII)_{175}$, $(VIII)_{179}$ and $(VIII)_{180}$, respectively) shown in Table 1 (for example, the compound (VIII) corresponding to Compound No. 148 is referred to as Compound $(VIII)_{148}$, and this Compound

13

(VIII)₁₄₈ means a compound wherein $R^2$ and $R^7$ are both $CH_3$, and $R^9$ is a corresponding 4-methylphenyl in the compound (VIII)).

The compound (IX) can be easily prepared, for example, by adding sodium hydrosulfide to the compound (VI) in water or an alcohol and heating the mixture under stirring.

As the compound (IX), there may be mentioned, for example, the respective compounds comprising the respective kinds of substituted groups corresponding to Compounds Nos. 144, 148, 153, 157, 158, 162, 164, 167, 168, 171, 175, 179 and 180 (which are referred to as Compounds (IX)₁₄₄, (IX)₁₄₈, (IX)₁₅₃, (IX)₁₅₇, (IX)₁₅₈, (IX)₁₆₂, (IX)₁₆₄, (IX)₁₆₇, (IX)₁₆₈, (IX)₁₇₁, (IX)₁₇₅, (IX)₁₇₉ and (IX)₁₈₀, respectively) shown in Table 1 (for example, the compound (IX) corresponding to Compound No. 148 is referred to as Compound (IX)₁₄₈, and this Compound (IX)₁₄₈ means a compound wherein $R^6$ is $OCH_3$ in the compound (IX)).

The reaction can be carried out by using the same solvent, base, reaction temperature and reaction time as mentioned in Preparation method 3.

PREPARATION METHOD 5

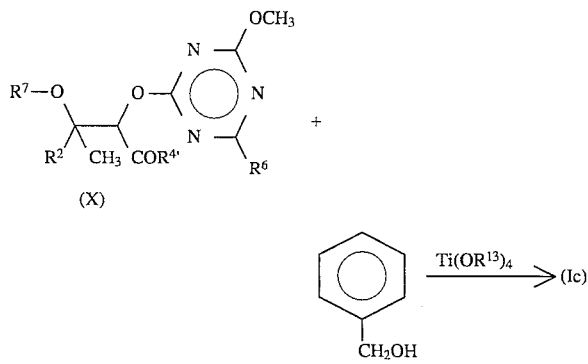

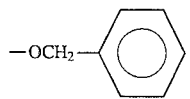

wherein $R^2$, $R^{4'}$, $R^6$ and $R^7$ each have the same meanings as defined above, and $R^{13}$ represents a lower alkyl group.

In general, the compound (Ic) can be easily prepared by subjecting a compound (X) to interesterification reaction with benzyl alcohol in a solvent using titanium tetraalkoxide as a catalyst.

The compound (X) can be easily prepared, for example, according to the above Preparation method 3.

As the compound (X), there may be mentioned, for example, the respective compounds comprising the respective kinds of substituted groups corresponding to Compounds Nos. 142, 146, 151, 155, 160, 166, 170, 173 and 177 (which are referred to as Compounds (X)₁₄₂, (X)₁₄₆, (X)₁₅₁, (X)₁₅₅, (X)₁₆₀, (X)₁₆₆, (X)₁₇₀, (X)₁₇₃ and (X)₁₇₇, respectively) shown in Table 1 (for example, the compound (X) corresponding to Compound No. 151 is referred to as Compound (X)₁₅₁, and this Compound (X)₁₅₁ means a compound wherein $R^2$ is $CH_3$, $R^7$ is $C_2H_5$, $R^{4'}$ is and $R^6$ is $OCH_3$ in the compound (X)).

The solvent is not particularly limited so long as it does not participate in the present reaction directly, and may include, for example, aromatic hydrocarbons such as benzene, toluene and xylene.

As the catalyst, there may be mentioned titanium tetraisopropoxide and titanium tetra-n-propoxide.

14

The preparation of the compound (Ic) can be carried out at a reaction concentration of 5 to 80%.

In the preparation method, the ratio of using the starting compound (X) and benzyl alcohol is that 1 to 3 moles, preferably 1.5 to 2 moles of the benzyl alcohol per mole of the starting compound (X).

The reaction temperature is not particularly limited so long as it is a boiling point of a solvent to be used or lower, but the reaction can be carried out generally at 70° to 150° C.

The reaction time varies depending on the above concentration and temperature, but may be generally carried out within 2 to 20 hours.

PREPARATION METHOD 6

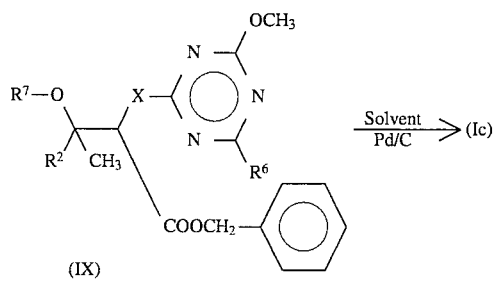

wherein $R^2$, $R^6$, $R^7$ and X each have the same meanings as defined above.

The compound (Ic) can be easily prepared by subjecting the compound (IX) to hydrogenolysis at normal pressure by using a palladium-carbon as a catalyst.

The compound (IX) can be easily prepared, for example, according to the above Preparation method 5.

As the compound (IX), there may be mentioned, for example, the respective compounds comprising the respective kinds of substituted groups corresponding to Compounds Nos. 143, 147, 152, 156, 161, 174 and 178 (which are referred to as Compounds (IX)₁₄₃, (IX)₁₄₇, (IX)₁₅₂, (IX)₁₅₆, (IX)₁₆₁, (IX)₁₇₄ and (IX)₁₇₈, respectively) shown in Table 1 (for example, the compound (IX) corresponding to Compound No. 147 is referred to as Compound (IX)₁₄₇, and this Compound (IX)₁₄₇ means a compound wherein $R^2$ and $R^7$ are both $CH_3$, $R^6$ is $OCH_3$ in the compound (IX)).

The solvent is not particularly limited so long as it does not participate in the present reaction directly, and may include, for example, chlorinated or not chlorinated aromatic hydrocarbons such as benzene, toluene, xylene and chlorobenzene; ethers such as tetrahydrofuran; alcohols such as metanol and ethanol.

As the catalyst, there may be mentioned palladium-carbon.

The preparation of the compound (Ic) can be carried out at a reaction concentration of 5 to 80%.

The reaction temperature is not particularly limited so long as it is a boiling point of a solvent to be used or lower, but the reaction can be carried out generally at 10° to 80° C., more preferably 20° to 50° C.

The reaction time varies depending on the above concentration and temperature, but may be generally carried out within 0.5 to 12 hours.

PREPARATION METHOD 7

The compound (Id') wherein $R^1$ in the formula (I) represents Y can be prepared by reacting the 3-hydroxy-2-pyrimidinylthioalkanoic acid derivative (Ie) with a halogenating agent.

The compound (Ie) can be prepared by reacting a corresponding ketone of the formula (X) with 2-pyrimidinylthioacetate of the formula (XI) in the presence of lithium in a solvent.

As the compound (X), commercially available ones may be used.

As the compound (X), there may be mentioned, for example, the respective compounds comprising the respective kinds of substituted groups corresponding to Compounds Nos. 181 to 195 (which are referred to as Compounds $(X)_{181}$ to $(X)_{195}$, respectively) shown in Table 1 (for example, the compound (X) corresponding to Compound No. 181 is referred to as Compound $(X)_{181}$, and this Compound $(X)_{181}$ means a compound wherein $R^2$ and $R^3$ are both $CH_3$).

The compound (XI) can be easily prepared by reacting a thioglycolate and 4,6-dimethoxy-2-methylsulfonylpyrimidine in the presence of a base in a solvent.

As the compound (XI), there may be mentioned, for example, the respective compounds comprising the respective kinds of substituted groups corresponding to Compounds Nos. 181 to 195 (which are referred to as Compounds $(XI)_{181}$ to $(XI)_{195}$, respectively) shown in Table 1 (for example, the compound (XI) corresponding to Compound No. 181 is referred to as Compound $(XI)_{181}$, and this Compound $(XI)_{181}$ means a compound wherein $R^5$ and $R^{6'}$ are both $OCH_3$ and $R^{4''}$ is $OC_2H_4Si(CH_3)_3$ in the compound (XI)).

The preparation of the compound (Ie) can be carried out at a reaction concentration of 10 to 80%. In the preparation method, the ratio of using the starting compounds (X) and (XI) is that 1 to 2 mole, preferably 1.1 to 1.2 mole of the starting compound (XI) per mole of the starting compound (X). The solvent may include, for example, dioxane, tetrahydrofuran (THF), diethylether and hexane. The reaction temperature is preferably −60° to −20° C. The reaction time may be within 1 to 3 hours under nitrogen stream while stirring.

As the compound (Ie), there may be mentioned, for example, the respective compounds comprising the respective kinds of substituted groups corresponding to Compounds Nos. 181 to 195 (which are referred to as Compounds $(Ie)_{181}$ to $(Ie)_{195}$, respectively) shown in Table 1 (for example, the compound (Ie) corresponding to Compound No. 181 is referred to as Compound $(Ie)_{181}$, and this Compound $(Ie)_{181}$ means a compound wherein $R^2$ and $R^3$ are both $CH_3$, $R^5$ and $R^{6'}$ are both $OCH_3$ and $R^{4''}$ is $OC_2H_5$ in the compound (Ie)).

In the preparation of the compound (Id'), as the halogenating agent, there may be mentioned thionyl chloride, thionyl bromide, phosphorus trichloride, phosphorus tribromide, phosphorus triiodide, hydroiodic acid, 1,1,2,2-tetrafluoroethylenediamine, tetrabutylphosphonium dihydrogen trifluoride, dimethylaminosulfur trifluoride and oxalic acid chloride. The reaction may be carried out at a reaction concentration of 5 to 80%. The ratio of the starting compound (Ie) and the halogenating agent is that 1 to 3 mole, preferably 1.1 to 1.5 mole of the halogenating agent per mole of the starting compound (Ie). When a solvent is used, it is not particularly limited so long as it is not reacted with the halogenating agent, and may include, for example, ethers such as diethyl ether, THF and dioxane; and halogenated aliphatic hydrocarbons such as methylene chloride and chloroform. The reaction temperature is not particularly limited but generally 0° to 100° C., preferably 0° to 50° C. The reaction time may vary depending on the above concentration and temperature, but generally 0.5 to 3 hours under stirring.

As the compound (Id'), there may be mentioned, for example, the respective compounds comprising the respective kinds of substituted groups corresponding to Compounds Nos. 196 to 218 (which are referred to as Compounds $(Id')_{196}$ to $(Id')_{218}$, respectively) shown in Table 1 (for example, the compound (Id') corresponding to Compound No. 196 is referred to as Compound $(Id')_{196}$, and this Compound $(Id')_{196}$ means a compound wherein $R^2$ and $R^3$ are both $CH_3$, $R^5$ and $R^{6'}$ are both $OCH_3$, $R^{4''}$ is $OC_2H_5$ and X is F in the compound (Id')).

PREPARATION METHOD 8

The compound (Id'') wherein $R^1$ in the formula (I) represents CN can be prepared by reacting the 3-halogeno-2-pyrimidinylthioalkanoic acid derivative (Id') with a cyanizing agent.

In the preparation of the compound (Id''), as the cyanizing agent, there may be mentioned sodium cyanide, potassium cyanide and copper cyanide. The reaction may be carried out at a reaction concentration of 10 to 80%. The ratio of the starting compound (Id') and the cyanizing agent is that 1 to 2 mole, preferably 1.1 to 1.5 mole of the cyanizing agent per mole of the starting compound (Id'). The solvent is not particularly limited so long as it dissolves a small amount of water, and may include, for example, DMF (N,N-dimethylfomamide), DMSO (dimethylsulfoxide), DMAC (N,N-dimethylacetamide), 1,3-dimethyl-2-imidazolidinone, acetone, acetonitrile, methanol and ethanol. The reaction temperature is not particularly limited but preferably 0° to 50° C. The reaction time may vary depending on the above concentration and temperature, but generally 0.5 to 3 hours under stirring.

As the compound (Id'') obtained by the above preparation method, there may be mentioned, for example, the respective compounds comprising the respective kinds of substituted groups corresponding to Compounds Nos. 220 to 232, 234 to 235, 241 to 243, 247 to 248, 253 to 255, 257 to 258, 261 to 262, 264 to 267, 269 to 271, 290 to 293 and 306 (which are referred to as Compounds 220 to 232, 234 to 235, 241 to 243, 247 to 248, 253 to 255, 257 to 258, 261 to 262, 264 to 267, 269 to 271, 290 to 293 and 306, respectively) shown in Table 1 (for example, the compound (Id'') corresponding to Compound No. 220 is referred to as Compound 220, and this Compound 220 means a compound wherein $R^2$ and $R^3$ are both $CH_3$ and $R^{4''}$, $R^5$ and $R^{6'}$ are all $OCH_3$ in the compound (Id'')).

PREPARATION METHOD 9

A compound represented by the following formula (Id'''):

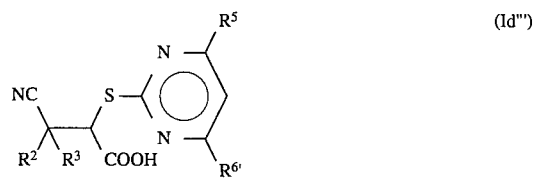

wherein $R^1$ in the formula (I) represents CN and $R^4$ represents hydroxyl group can be prepared by reacting the 3-cyano- 2-pyrimidinylthioalkanoic acid ester (Id'') with a base in a solvent.

In the preparation of the compound (Id'''), as the base, there may be mentioned sodium hydroxide and potassium hydroxide. The reaction may be carried out at a reaction concentration of 10 to 80%. The ratio of the starting compound (Id'') and the base is that 1 to 2 mole, preferably 1 to 1.2 mole of the base per mole of the starting compound (Id''). The solvent is not particularly limited so long as it dissolves a small amount of water, and may include, for example, DMF, DMSO, DMAC, 1,3-dimethyl-2-imidazolidinone, acetone, acetonitrile, methanol and ethanol. The reaction temperature is not particularly limited but preferably 0° to 60° C. The reaction time may vary depending on the above concentration and temperature, but generally 1 to 6 hours under stirring.

As the compound (Id''') obtained by the above preparation method, there may be mentioned, for example, the respective compounds comprising the respective kinds of substituted groups corresponding to Compounds Nos. 219, 252 and 260 (which are referred to as Compounds 219, 252 and 260, respectively) shown in Table 1 (for example, the compound (Id''') corresponding to Compound No. 219 is referred to as Compound 219, and this Compound 219 means a compound wherein $R^2$ and $R^3$ are both $CH_3$, $R^5$ and $R^{6'}$ are both $OCH_3$ and $R^{4'''}$ is OH in the compound (Id''')).

PREPARATION METHOD 10

The compound (Id) can be prepared by reacting the compound (Id''') with an alcohol, a thiol or an amine in a solvent existing a condensing agent in the presence or absence of a base with a cyanizing agent.

In the preparation of the compound (Id), as the condensing agent, there may be mentioned DCC (dicyclohexylcarbodiimide), WSC (1-ethyl-3-(3-dimethylaminopropyl) carbodiimide hydrochloride), carbonyldiimidazole and diethyl cyanophosphate. The reaction may be carried out at a reaction concentration of 10 to 80%. The ratio of the starting compound (Id''') and the condensing agent is that 1 to 2 mole, preferably 1 to 1.1 mole of the condensing agent per mole of the starting compound (Id'''). As the base, there may be mentioned triethylamine and sodium hydride and they may be added to the starting compound (Id''') in an amount of 1 to 2 mole, preferably 1 to 1.2 mole per mole of the starting compound (Id'''). The solvent is not particularly limited so long as it is non-aqueous one, and preferably includes methylene chloride, chloroform, toluene, benzene, THF and ethyl ether. The reaction temperature is not particularly limited but preferably 0° C. to room temperature. The reaction time may vary depending on the above concentration and temperature, but generally 0.5 to 6 hours under stirring.

As the compound (Id) obtained by the above preparation method, there may be mentioned, for example, the respective compounds comprising the respective kinds of substituted groups corresponding to Compounds Nos. 220 to 243, 247 to 248, 251, 253 to 258, 261 to 267, 269 to 281 and 289 to 304 (which are referred to as Compounds 220 to 243, 247 to 248, 251, 253 to 258, 261 to 267, 269 to 273, 276 to 281 and 289 to 304, respectively) shown in Table 1 (for example, the compound (Id) corresponding to Compound No. 241 is referred to as Compound 241, and this Compound 241 means a compound wherein $R^1$ is CN, $R^2$ and $R^3$ are both $CH_3$, $R^{4'''}$ is $NHSO_2CH_3$ and $R^5$ and $R^{6'}$ are both $OCH_3$ in the compound (Id)).

PREPARATION METHOD 11

The compound (Id) can be prepared by reacting a metal salt or an amine salt of a compound represented by the formula (XII):

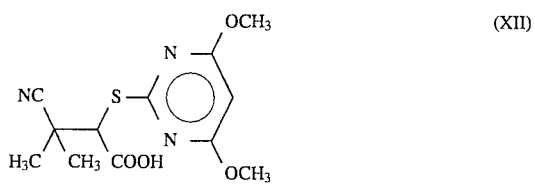

with a halogen-substituted alkyl compound in the presence or absence of a catalyst and in the presence of a base.

In the preparation method, as the catalyst, there may be mentioned a crown ether (e.g. 18-crown-6-ether) and a quaternary ammonium salt (e.g. tetrabutylammonium bromide); and as the base, there may be mentioned sodium hydroxide, potassium hydroxide, sodium hydride, metal sodium and triethylamine. As the halogen-substituted alkyl compound, there may be mentioned methoxymethyl chloride, methoxyethoxymethyl chloride, pivaloyloxymethyl chloride and methylthiomethyl chloride. The reaction may be carried out at a reaction concentration of 10 to 80%. The ratio of the starting compound (XII) and the base is that 1 to 2 mole, preferably 1 to 1.1 mole of the base per mole of the starting compound (XII). The solvent is not particularly limited, and may include, for example, DMF, DMSO, toluene, benzene, methylene chloride, chloroform, acetonitrile, THF and ethyl ether. The reaction temperature is not particularly limited but preferably 0° to 100° C. The reaction time may vary depending on the above concentration and temperature, but generally 0.5 to 6 hours under stirring.

As the compound (Id) obtained by the above preparation method, there may be mentioned, for example, the respective compounds comprising the respective kinds of substituted groups corresponding to Compounds Nos. 244 to 246, 249 to 250, 268, 274 to 275, 282 to 287 and 305 (which are referred to as Compounds 244 to 246, 249 to 250, 268, 274 to 275, 282 to 287 and 305, respectively) shown in Table 1 (for example, the compound (Id) corresponding to Compound No. 244 is referred to as Compound 244, and this Compound 244 means a compound wherein $R^{1'}$ is CN, $R^2$ and $R^3$ are both $CH_3$, $R^{4'''}$ is $OCH_2OCH_3$, $R^5$ and $R^{6'}$ are both $OCH_3$ in the compound (Id)).

The herbicide containing the compound (I) as an active ingredient has high selectivity and also shows excellent herbicidal effect.

That is, the herbicide of the present invention shows excellent herbicidal effect on annual weeds and perennial weeds grown in paddy fields and upland fields, and its herbicidal effect is particularly remarkable in annual grass weeds (e.g. crabgrass (manna-grass), barnyardgrass and foxtail (green panicum)), annual broad-leaved weeds (e.g. morning glory, common lambsquarter (white goosefoot), livid amaranthus and velvetleaf) and perennial weeds (e.g. Johnson grass, bulrush and flatstage).

The herbicide of the present invention shows excellent herbicidal effect on the weeds described above, but does not give chemical damage on field crops (e.g. cotton) at a concentration for such a treatment.

The herbicide of the present invention contains the compound (I) as an active ingredient(s).

The compound (I) can be used singly, but may be preferably used by mixing with a carrier, a surfactant, a dispersant and an auxiliary (for example, prepared as a composition such as a dust, an emulsion, a fine granule, a granule, a wettable powder, an oily suspension and an aerosol) according to a conventional method.

As the carrier, there may be mentioned, for example, a solid carrier such as talc, mica, bentonite, clay, kaolin, diatomaceous earth, white carbon, vermiculite, dolomite, zeolite, slaked lime, siliceous sand, silicic anhydride, ammonium sulfate, urea, wood powder, starch and cellulose; a liquid carrier such as hydrocarbons (kerosine and mineral oil), aromatic hydrocarbons (benzene, toluene and xylene), chlorinated hydrocarbons (chloroform and carbon tetrachloride), ethers (dioxane and tetrahydrofuran), ketones (acetone, cyclohexanone and isophorone), esters (ethyl acetate, ethylene glycol acetate and dibutyl maleate), alcohols (methanol, n-hexanol and ethylene glycol), polar solvents (dimethylformamide and dimethylsulfoxide) and water; and a gas carrier such as air, nitrogen, carbonic acid gas and freon (in the case of a gas carrier, mixed spray can be carried out).

As the surfactant which can be used for improving attachment of the present herbicide to and absorption thereof in plants, and improving characteristics such as dispersion, emulsification and spreading of the herbicide, there may be mentioned nonionic, anionic, cationic or amphoteric surfactants (e.g. alcohol sulfates, alkylsulfonates, lignin sulfonates and polyoxyethylene glycol ethers). Further, for improving properties of preparation, carboxymethyl cellulose, polyethylene glycol or gum arabic can be used as an auxiliary.

In preparation of the present herbicide, in addition to the above carrier, surfactant, dispersant and auxiliary, other agricultural chemicals (a fungicide and an insecticide), a fertilizer and a soil conditioner can be used singly or in a suitable combination, respectively, depending on the respective purposes.

When the compound (I) of the present invention is made into preparations, the concentration of the active ingredient is generally 1 to 50% by weight in an emulsion, generally 0.3 to 25% by weight in a dust, generally 1 to 90% by weight in a wettable powder, generally 0.5 to 5% by weight in a granule, generally 0.5 to 5% by weight in an oily dispersion, and generally 0.1 to 5% by weight in an aerosol.

These preparations can be provided for various uses by diluting them to have a suitable concentration and spraying them to stems and/or leaves of plants, soil and paddy field surface, or by applying them directly thereto, depending on the respective purposes.

EXAMPLES

The present invention is described in detail by referring to Examples, but the scope of the present invention is not limited by these Examples.

Example 1

(1) Synthesis of
1-(3-ethoxy-2-(4,6-dimethoxypyrimidin-2-yl)oxy-
3-methylbutyryl)imidazole (Compound 12)

In 100 ml of methylene chloride was dissolved 19.4 g (0.12 mol) of N,N-carbonyldiimidazole, and the mixture was maintained at 5° C. To the mixture was added dropwise 30.0 g (0.1 mol) of 3-ethoxy-2-(4,6-dimethoxypyrimidin-2-yl)oxy- 3-methylbutanoic acid dissolved in 100 ml of an N,N-dimethylformamide (DMF) solution, and the mixture was stirred at room temperature for 0.5 hour.

After completion of the stirring, the methylene chloride layer was washed with water and dried over sodium sulfate, and methylene chloride was removed under reduced pressure. The crystals obtained were washed with n-hexane to obtain 29.8 g (yield: 85%) of the title compound as white crystals.

(2) Synthesis of
1-(2-(4,6-dimethoxy-2-yl)thio-3-methoxy-
3-methylbutyryl)imidazole (Compound 7)

In 150 ml of methylene chloride was dissolved 19.4 g (0.12 mol) of N,N-carbonyldiimidazole, and the mixture was maintained at 5° C. To the mixture was added dropwise 30.2 g (0.1 mol) of 2-(4,6-dimethoxy-2-yl)thio-3-methoxy-3-methylbutanoic acid dissolved in 100 ml of a DMF solution, and the mixture was stirred at 5° C. for 1 hour.

After completion of the stirring, the reaction mixture was added to 100 ml of water and extracted with ethyl acetate. The ethyl acetate layer was washed with a saturated saline solution and dried over sodium sulfate, and ethyl acetate was removed under reduced pressure. The crystals obtained were washed with n-hexane to obtain 30.0 g (yield: 85%) of the title compound as white crystals.

(3) Synthesis of
2-(4,6-dimethoxypyrimidin-2-yl)thio-3-methoxy-
3-methyl-N-methylsulfonylbutanoic acid amide
(Compound 47)

In 50 ml of N,N-dimethylformamide (DMF) was suspended sodium hydride (0.1 mol, 4 g in which 60% thereof was dissolved in oil), and to the suspension was added dropwise 9.5 g (0.1 mol) of methanesulfonamide dissolved in 50 ml of a DMF solution. The mixture was stirred for 2 hours. After completion of the stirring, 35.2 g (0.1 mol) of 1-(2-( 4,6-dimethoxypyrimidin-2-yl)thio-3-methoxy-3-methylbutyryl)imidazole dissolved in 100 ml of DMF was added dropwise to the mixture. After completion of the dropwise addition, the mixture was stirred at room temperature for 1 hour.

To the reaction mixture were added water and 1N hydrochloric acid (300 ml) and the mixture was extracted with ethyl acetate. The ethyl acetate layer was washed with a saturated saline solution and dried over sodium sulfate, and ethyl acetate was removed under reduced pressure. The residue obtained was isolated by column chromatography (Wako gel C-200, (trade name, manufactured by Wako Junyaku K.K.), eluted by n-hexane: ethyl acetate: methanol= 1:1:0.1) to obtain 28.4 g (yield: 75%) of the title compound as white crystals.

(4) Synthesis of
3-ethoxy-2-(4,6-dimethoxypyrimidin-2
-yl)oxy-3-methyl-N-methylsulfonylbutanoic acid
amide (Compound 67)

In 50 ml of N,N-dimethylformamide (DMF) was dissolved 19.4 g (0.12 mol) of carbonyldiimidazole, and the mixture was maintained at 5° C. To the mixture was added dropwise 30 g (0.1 mol) of 3-ethoxy-2-(4,6-dimethoxypyrimidin-2-yl)oxy-3-methylbutanoate dissolved in 100 ml of a DMF solution. After completion of the dropwise addition, the mixture was stirred for 0.5 hour. To the mixture were added 9.5 g (0.1 mol) of methanesulfonamide and further sodium hydride (0.1 mol, 4 g in which 60% thereof was dissolved in oil) at 0° C. The mixture was stirred for 1 hour.

To the reaction mixture were added water and 1N hydrochloric acid (300 ml) and the mixture was extracted with ethyl acetate. The ethyl acetate layer was washed with a saturated saline solution and dried over sodium sulfate, and ethyl acetate was removed under reduced pressure. The residue obtained was isolated by column chromatography (Wako gel C-200, (trade name, manufactured by Wako Junyaku K.K.), eluted by n-hexane:ethyl acetate:methanol=1:1:0.1) to obtain 30.0 g (yield: 80%) of the title compound as white crystals.

(5) Synthesis of ethyl 2-(4,6-dimethoxy-s-triazin-2-yl)oxy-3-ethoxy-3-methylbutanoate (Compound 154)

The compound (Ic) of the present invention was synthesized according to the method described in (Preparation method 3).

That is, in 40 ml of ethanol was dissolved 14.4 g (0.1 mol) of ethyl 2,3-epoxy-3-methylbutanoate, and then 0.5 ml of sulfuric acid was added thereto as a catalyst. The mixture was stirred at 30° C. for 2 hours.

Subsequently, excessive ethanol was removed under reduced pressure, and the residue was applied to column chromatography (Wako gel C-200 (trade name, manufactured by Wako Junyaku K.K.), eluted by n-hexane:ethyl acetate=7:3) to obtain ethyl 3-ethoxy-2-hydroxy-3-methylbutanoate. This product was added at 5° C. to 0.1 mol of sodium hydride (60% thereof was dissolved in 4 g of oil) suspended in 100 ml of tetrahydrofuran, and the mixture was stirred for 30 minutes. After completion of the stirring, to the mixture was added dropwise 17.5 g (0.1 mol) of 2-chloro-4,6-dimethoxy-s-triazine dissolved in 50 ml of tetrahydrofuran, and the mixture was stirred at 20° C. for 1 hour.

The reaction mixture was added to water and extracted with ethyl acetate. The ethyl acetate layer was washed with a saturated saline solution and dried over sodium sulfate, and ethyl acetate was removed under reduced pressure. The residue obtained was isolated by column chromatography (Wako gel C-200 (trade name, manufactured by Wako Junyaku K.K.), eluted by n-hexane:ethyl acetate=3:1) to obtain 26.3 g (yield: 80%) of the title compound as a colorless oily product.

(6) Synthesis of benzyl 2-(4,6-dimethoxy-s-triazin-2-yl)oxy-3-ethoxy-3-methylbutanoate (Compound 155)

The title compound (Ic) was synthesized according to the method described in (Preparation method 5).

That is, in 200 ml of toluene were dissolved 32.9 g (0.1 mol) of Compound 154 prepared in the above (5) and 16.2 g (0.15 mol) of benzyl alcohol. To the solution was added 3 ml of titanium tetraisopropoxide as a catalyst. The mixture was refluxed by heating for 6 hours while removing ethanol liberated during reflux.

Subsequently, the reaction mixture was cooled to room temperature. The toluene layer was washed with water, and toluene was removed under reduced pressure. The residue obtained was isolated by column chromatography (Wako gel C-200 (trade name, manufactured by Wako Junyaku K.K.), eluted by n-hexane:ethyl acetate=3:1) to obtain 33.3 g (yield: 85%) of the title compound as a colorless oily product.

(7) Synthesis of 2-(4,6-dimethoxy-s-triazin-2-yl)oxy-3-ethoxy-3-methylbutanoic acid (Compound 156)

The compound (Ic) of the present invention was synthesized according to the method described in (Preparation method 6).

That is, in 200 ml of ethanol were dissolved 39.2 g (0.1 mol) of Compound 155 prepared in the above (6), and 0.5 g of palladium carbon was added thereto as a catalyst. The mixture was stirred at room temperature (20° C.) for 1 hour while blowing hydrogen therein. Subsequently, the catalyst was removed by filtration, and the mother liquor was concentrated to obtain 28.6 g (yield: 95%) of the title compound as a colorless oily product.

(8) Synthesis of 2-(4,6-dimethoxy-s-triazin-2-yl)thio-3-ethoxy-3-methylbutanoic acid (Compound 157)

The title compound (Ic) was synthesized according to the method described in (Preparation method 3).

That is, in 1N sodium hydroxide was dissolved 17.8 g (0.1 mol) of 3-ethoxy-2-mercapto-3-methylbutanoic acid. To the solution was added a solution of 17.5 g (0.1 mol) of 2-chloro-4,6-dimethoxy-s-triazine dissolved in 100 ml of acetone, and the mixture was stirred at room temperature (20° C.) for 1 hour.

The reaction mixture was added to 100 ml of 5N hydrochloric acid aqueous solution and extracted with ethyl acetate. The ethyl acetate layer was washed with a saturated saline solution and dried over sodium sulfaste, and ethyl acetate was removed under reduced pressure. The residue obtained was isolated by column chromatography (Wako gel C-200 (trade name, manufactured by Wako Junyaku K.K.), eluted by n-hexane:ethyl acetate:acetic acid=1:1:0.1) to obtain 23.7 g (yield: 75%) of the title compound as a colorless transparent oily product.

(9) Synthesis of 2-(4,6-dimethoxy-s-triazin-2-yl)thio-3-methoxy-3-methylbutanoic acid (Compound 148)

The title compound (Ic) was synthesized according to the method described in (Preparation method 4).

That is, to 150 ml of N,N'-dimethylformamide were added 30.2 g (0.1 mol) of 3-methoxy-3-methyl-2-paratoluenesulfonyloxybutanoic acid and 17.3 g (0.1 mol) of 4,6-dimethoxy-2-mercapto-s-triazine, and further, 13.8 (0.1 mol) of potassium carbonate was added thereto. The mixture was stirred at 50° C. for 2 hours.

The reaction mixture was added to water and extracted with ethyl acetate. The ethyl acetate layer was washed with a saturated saline solution and dried over sodium sulfate, and ethyl acetate was removed under reduced pressure. The residue obtained was isolated by column chromatography (Wako gel C-200 (trade name, manufactured by Wako Junyaku K.K,), eluted by n-hexane:ethyl acetate:acetic acid=1:1:0.1) to obtain 24.2 g (yield: 80%) of the title compound as white crystals.

(10) Synthesis of ethyl 2-(4,6-dimethoxypyrimidin-2-yl)thio-3-hydroxy-3-methylbutanoate (Compound (Ie) 181)

The title compound was synthesized according to the synthetic method of Compound (Ie) described in (Preparation method 7).

That is, in 300 ml of tetrahydrofuran (THF) was dissolved 25.8 g (0.1 mol) of ethyl (4,6-dimethoxypyrimidin-2-yl)thioacetate. To the solution was added dropwise 110 ml (0.11 mol) of a bis(trimethylsilyl)lithium amide—1M THF solution at −78° C. under nitrogen gas stream, and then 6.4 g (0.11 mol) of acetone was added thereto. The mixture was stirred for 1 hour. Subsequently, the reaction mixture was elevated to a temperature of 0° C. The mixture was poured into water, and 500 ml of ethyl ether was added thereto. The ethyl ether layer was extracted, washed with water and dried. THF and ethyl ether was removed under reduced pressure, and the residue obtained was isolated by column chromatography (Wako gel C-200 (trade name, manufactured by Wako Junyaku K.K.), eluted by n-hexane:ethyl acetate=5:1) to obtain 24.6 g (yield: 78%) of the title compound as a colorless transparent viscous liquid.

Physical property: reflective index at 20° C. was 1.5230.

(11) Synthesis of ethyl 3-chloro-2-(4,6-dimethoxypyrimidin-2-yl)thio-3-methylbutanoate (Compound 215)

The compound (Id) was synthesized according to (Preparation method 7).

That is, in 100 ml of ethyl ether was dissolved 16.8 g (53 mmol) of Compound $(Ie)_{181}$ obtained in the above (10), and to the solution was added dropwise 6.5 g (55 mmol) of thionyl chloride at room temperature. The mixture was stirred for 1 hour. Subsequently, the reaction mixture was poured into ice water and washed with water, and further washed with water twice, followed by drying. Ethyl ether was removed under reduced pressure, and the residue obtained was isolated by column chromatography (Wako gel C-200 (trade name, manufactured by Wako Junyaku K.K.), eluted by n-hexane:ethyl acetate=8:1) to obtain 14.2 g (yield: 80%) of the title compound as white crystals.

(12) Synthesis of ethyl 3-cyano-2-(4,6-dimethoxypyrimidin-2-yl)thio-3-methylbutanoate (Compound 221)

The compound (Id) was synthesized according to (Preparation method 7).

That is, in 30 ml of DMF was dissolved 3.4 g (10 mmol) of Compound 215 obtained in the above (11), and to the solution was added 12 mmol of a sodium cyanide solution (a solution of 0.6 g of sodium cyanide dissolved in 2 ml of water). The mixture was stirred at 60° C. for 3 hours. Subsequently, the reaction mixture was poured into water and extracted with 100 ml of toluene. The toluene layer was washed with water 5 times and dried, and toluene was removed under reduced pressure.

The oily product obtained was isolated by column chromatography (Wako gel C-200 (trade name, manufactured by Wako Junyaku K.K.), eluted by n-hexane:ethyl acetate=8:1) to obtain 2.1 g (yield: 65%) of the title compound as white crystals.

(13) Synthesis of 3-cyano-2-(4,6-dimethoxypyrimidin-2-yl)thio-3-methylbutanoic acid (Compound 219)

The compound (Id) was synthesized according to (Preparation method 9).

That is, in 10 ml of acetone was dissolved 1.0 g (3 mmol) of Compound 221 obtained in the above (12), and to the solution was added a sodium hydroxide solution (a solution of 0.2 g of sodium hydroxide dissolved in 10 ml of water).

The mixture was stirred at room temperature for 5 hours. Subsequently, the reaction mixture was poured into water, neutralized with a 1N hydrochloric acid solution and extracted with ethyl ether. The ethyl ether layer was washed with water and dried, and ethyl ether was removed under reduced pressure to obtain 0.7 g (yield: 78%) of the title compound as white crystals.

(14) Synthesis of propyl 3-cyano-2-(4,6-dimethoxypyrimidin-2-yl)thio-3-methylbutanoate (Compound 222)

The compound (Id) was synthesized according to (Preparation method 10).

That is, in 30 ml of dried methylene chloride were dissolved 0.6 g (2 mmol) of Compound 219 obtained in the above (13) and 0.2 g (3 mmol) of propanol, and to the solution was added 0.4 g (2 mmol) of WSC at 5° C. The mixture was stirred for 30 minutes. Subsequently, the reaction mixture was poured into water, washed with water and dried, and methylene chloride was removed under reduced pressure.

The oily product obtained was isolated by column chromatography (Wako gel C-200 (trade name, manufactured by Wako Junyaku K.K.), eluted by n-hexane:ethyl acetate=8:1) to obtain 0.5 g (yield: 74%) of the title compound as white crystals.

(15) Synthesis of 3-cyano-2-(4,6-dimethoxypyrimidin-2-yl)thio-3-methylbutyryl-1-imidazole (Compound 240)

The compound (Id) was synthesized according to (Preparation method 10).

That is, in 30 ml of dried methylene chloride was dissolved 1.0 g (3.4 mmol) of Compound 219 obtained in the above (13). At room temperature, 0.6 g (3.4 mmol) of carbonyldiimidazole was added to the solution, and the mixture was stirred for 30 minutes. Further, 5 ml of water was added thereto, and the mixture was stirred for 5 minutes. Subsequently, from the reaction mixture, water was removed by using a filter paper for separation, and methylene chloride was removed under reduced pressure to obtain 1.1 g (yield: 90%) of the title compound as pale brown crystals.

(16) Synthesis of 3-cyano-2-(4,6-dimethoxypyrimidin-2-yl)thio-3-methyl-N-methylsulfonylbutanoic acid amide (Compound 241)

The compound (Id) was synthesized according to (Preparation method 10).

That is, in 20 ml of DMF were dissolved 0.8 g (2.2 mmol) of Compound 240 obtained in the above (13) and 0.3 g (3 mmol) of methanesulfonamide, and to the solution was added 0.1 g (25 mmol) of sodium hydride at 5° C. The mixture was stirred at room temperature for 1 hour. Subsequently, the reaction mixture was poured into water, neutralized with a citric acid aqueous solution and extracted by 80 ml of chloroform. The chloroform layer was washed with water 5 times and dried, and chloroform was removed under reduced pressure to obtain a semisolid material.

To the semisolid material was added 30 ml of hexane, and the mixture was left to stand. The crystals obtained were collected by filtration and dried to obtain 7.1 g (yield: 87%) of the title compound as white crystals.

(17) Synthesis of potassium 3-cyano-2-(4,6-dimethoxypyrimidin-2-yl)thio-3-methylbutanoate (Compound 245)

The compound (Id) was synthesized according to (Preparation method 11).

That is, in 20 ml of methanol was dissolved 0.23 g of powdered potassium hydroxide, and in the solution was dissolved 1.0 g (3.4 mmol) of Compound 219 obtained in the above (13) dissolved in 20 ml of methanol. The mixture was stirred at room temperature for 30 minutes. Subsequently, methanol was removed under reduced pressure to obtain a white solid material.

The solid material was added to 30 ml of toluene, and washed sufficiently. Toluene was removed by filtration, and the residue was dried to obtain 1.0 g (yield: 98%) of the title compound as white crystals.

(18) Synthesis of (t-butylcarbonyloxymethyl)3-cyano-2-(4,6-dimethoxypyrimidin-2-yl)thio-3-methylbutanoate (Compound 246)

The compound (Id) was synthesized according to (Preparation method 11).

That is, in 50 ml of toluene were dissolved 1.0 g (3 mmol) of Compound 245 obtained in the above (17), 0.5 g (3.3 mmol) of chloromethyl pivalate, 1.0 g (6 mmol) of potassium iodide and 0.1 g of crown ether, and the mixture was refluxed by boiling for 5 hours. Subsequently, the reaction mixture was poured into water, washed with water and dried, and toluene was removed under reduced pressure to obtain a pale yellow oily product.

The oily product obtained was isolated by column chromatography (Wako gel C-200 (trade name, manufactured by Wako Junyaku K.K.), eluted by n-hexane:ethyl acetate=1:8) to obtain 0.9 g (yield: 73%) of a colorless transparent oily product.

(19) Syntheses of other compounds (I) in Table 1

In the same manner as in either of the synthetic methods (1) to (11), the title compounds (I) as shown in Table 1 were obtained.

TABLE 1

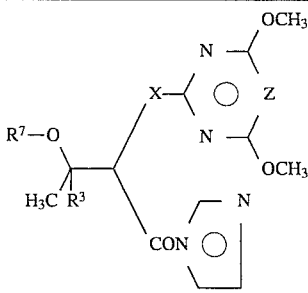

| Compound No. | $R^7$ | $R^3$ | X | Z | Physical property |
|---|---|---|---|---|---|
| 1 | CH$_3$ | H | O | CH | |
| 2 | " | " | " | N | |
| 3 | " | " | S | CH | |
| 4 | " | " | " | N | |
| 5 | " | CH$_3$ | O | CH | m.p. 129–131° C. |
| 6 | " | " | " | N | m.p. 93–95° C. |
| 7 | " | " | S | CH | m.p. 114–118° C. |
| 8 | " | " | " | " | m.p. 74–76° C. |
| 9 | C$_2$H$_5$ | H | O | CH | |
| 10 | " | " | S | " | $n_D^{24.0}$ 1.5298 |
| 11 | " | " | " | N | m.p. 113–116° C. |
| 12 | " | CH$_3$ | O | CH | m.p. 84–88° C. |
| 13 | " | " | " | N | |
| 14 | " | " | S | CH | $n_D^{19.2}$ 1.5411 |
| 15 | C$_2$H$_5$ | CH$_3$ | S | N | m.p. 87–89° C. |
| 16 | n-C$_3$H$_7$ | " | O | CH | m.p. 98–99° C. |
| 17 | " | " | S | " | |
| 18 | " | " | " | N | |
| 19 | CH$_2$=CH—CH$_2$— | H | O | CH | m.p. 112–113° C. |
| 20 | " | " | S | " | |
| 21 | " | " | " | N | |
| 22 | " | CH$_3$ | O | CH | m.p. 102–103° C. |
| 23 | " | " | S | " | m.p. 99–100° C. |
| 24 | " | " | " | N | m.p. 97–98° C. |
| 25 | HC≡C—CH$_2$— | H | O | CH | m.p. 98–100° C. |

TABLE 1-continued

| | | | | | | |
|---|---|---|---|---|---|---|
| 26 | " | " | S | " | | $n_D^{25.6}$ 1.5194 |
| 27 | " | " | " | N | | |
| 28 | " | CH$_3$ | O | CH | | m.p. 90~92° C. |
| 29 | " | " | S | " | | m.p. 69~70° C. |
| 30 | " | " | " | N | | m.p. 83~85° C. |
| 31 | ClCH$_2$CH$_2$— | " | O | CH | | m.p. 96~97° C. |
| 32 | ClCH$_2$CH$_2$— | CH$_3$ | O | N | | m.p. 103~105° C. |
| 33 | " | " | S | CH | | m.p. 83~84° C. |
| 34 | " | " | " | N | | |
| 35 | CNCH$_2$CH$_2$— | " | O | CH | | |
| 36 | " | " | " | N | | |
| 37 | " | " | S | CH | | |
| 38 | " | " | " | N | | |

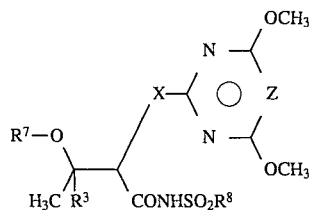

| Compound No. | R$^7$ | R$^3$ | R$^8$ | X | Z | Physical property |
|---|---|---|---|---|---|---|
| 39 | CH$_3$ | H | CH$_3$ | O | CH | |
| 40 | " | " | " | " | N | |
| 41 | " | " | " | S | CH | m.p. 123~126° C. |
| 42 | " | " | " | " | N | |
| 43 | " | " | C$_2$H$_5$ | O | CH | |
| 44 | " | " | " | S | " | |
| 45 | CH$_3$ | CH$_3$ | CH$_3$ | O | CH | m.p. 126~127° C. |
| 46 | " | " | " | " | N | $n_D^{23.8}$ 1.4933 |
| 47 | " | " | " | S | CH | m.p. 97~98° C. |
| 48 | " | " | " | " | N | m.p. 98~101° C. |
| 49 | " | " | C$_2$H$_5$ | O | CH | m.p. 103~105° C. |
| 50 | " | " | " | S | " | m.p. 73~75° C. |
| 51 | " | " | " | " | N | oily product |
| 52 | " | " | n-C$_3$H$_7$ | O | CH | |
| 53 | " | " | " | S | " | $n_D^{24.9}$ 1.5334 |
| 54 | " | " | i-C$_3$H$_7$ | O | " | |
| 55 | " | " | " | S | " | $n_D^{23.7}$ 1.3310 |
| 56 | " | " | n-C$_4$H$_9$ | O | " | |
| 57 | " | " | " | S | " | $n_D^{25.8}$ 1.5243 |
| 58 | " | " | ⌬ (phenyl) | O | " | |
| 59 | " | " | ⌬-Cl (chlorophenyl) | " | " | |
| 60 | " | " | ⌬-CH$_3$ (methylphenyl) | " | " | |
| 61 | C$_2$H$_5$ | H | CH$_3$ | " | " | m.p. 112~116° C. |
| 62 | " | " | " | S | " | $n_D^{23.2}$ 1.5324 |
| 63 | C$_2$H$_5$ | H | CH$_3$ | S | N | $n_D^{23.7}$ 1.5056 |
| 64 | " | " | C$_2$H$_5$ | O | CH | $n_D^{23.4}$ 1.5028 |
| 65 | " | " | " | S | " | $n_D^{26.0}$ 1.5266 |
| 66 | " | " | " | " | N | |
| 67 | " | CH$_3$ | CH$_3$ | O | CH | m.p. 58~60° C. |
| 68 | " | " | " | S | " | $n_D^{21.8}$ 1.5253 |
| 69 | " | " | " | " | N | Oily product |
| 70 | " | " | C$_2$H$_5$ | O | CH | m.p. 59~62° C. |
| 71 | " | " | n-C$_3$H$_7$ | " | " | m.p. 79~81° C. |
| 72 | " | " | i-C$_3$H$_7$ | " | " | m.p. 117~118° C. |
| 73 | " | " | n-C$_4$H$_9$ | " | " | m.p. 72~74° C. |

TABLE 1-continued

| | | | | | | |
|---|---|---|---|---|---|---|
| 74 | " | " | 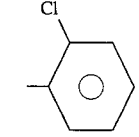 Cl | " | " | m.p. 120~121° C. |
| 75 | " | " | 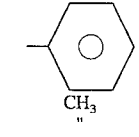 | " | " | Oily product |
| 76 | n-C₃H₇ | " | CH₃ | " | " | m.p. 58~59° C. |
| 77 | " | " | " | S | " | m.p. 104~106° C. |
| 78 | " | " | " | " | N | m.p. 110~112° C. |
| 79 | i-C₃H₇ | H | CH₃ | O | CH | |
| 80 | CH₂=CHCH₂— | " | " | " | " | m.p. 122~125° C. |
| 81 | " | " | " | S | " | m.p. 98~101° C. |
| 82 | " | " | " | " | N | |
| 83 | " | CH₃ | " | O | CH | m.p. 60~61° C. |
| 84 | " | " | " | S | " | $n_D^{24.0}$ 1.5342 |
| 85 | " | " | " | " | N | $n_D^{22.6}$ 1.5332 |
| 86 | HC≡CCH₂— | H | " | O | CH | m.p. 128~131° C. |
| 87 | " | " | " | S | " | |
| 88 | " | " | " | " | N | |
| 89 | " | CH₃ | " | O | CH | m.p. 62~65° C. |
| 90 | " | " | " | S | " | m.p. 131~134° C. |
| 91 | " | " | " | " | N | |
| 92 | ClCH₂CH₂— | " | " | O | CH | m.p. 93~94° C. |
| 93 | " | " | " | S | " | $n_D^{22.6}$ 1.5451 |
| 94 | " | " | " | O | N | $n_D^{21.6}$ 1.4916 |
| 95 | " | " | " | S | " | oily product |
| 96 | CNCH₂CH₂— | " | " | O | CH | m.p. 155~158° C. |
| 97 | CNCH₂CH₂— | CH₃ | CH₃ | S | CH | |
| 98 | " | " | " | " | N | |
| 99 | CH₃ | " | n-C₃H₇ | " | " | $n_D^{24.9}$ 1.5178 |
| 100 | " | " | i-C₃H₇ | " | " | $n_D^{24.5}$ 1.5190 |
| 101 | " | " | n-C₄H₉ | " | " | $n_D^{24.6}$ 1.5140 |
| 102 | " | " | 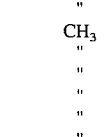 | " | CH | $n_D^{25.5}$ 1.5470 |
| 103 | " | " | " | " | N | m.p. 47~50° C. |
| 104 | " | " |  Cl | " | CH | m.p. 131~135° C. |
| 105 | " | " | " | " | N | oily product |
| 106 | " | " | 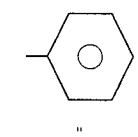 Cl | " | CH | m.p. 49~52° C. |
| 107 | " | " | " | " | N | m.p. 51~54° C. |
| 108 | " | " | 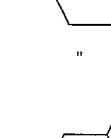—Cl | " | CH | m.p. 89~93° C. |
| 109 | " | " | " | " | N | m.p. 68~72° C. |
| 110 | " | " | 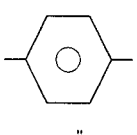 H₃C | " | CH | m.p. 44~49° C. |

TABLE 1-continued

| | | | | | | |
|---|---|---|---|---|---|---|
| 111 | " | " | " | " | N | m.p. 38–41° C. |
| 112 | " | " | 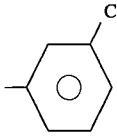 (2,4-dimethylphenyl) | " | CH | m.p. 42–46° C. |
| 113 | " | " | " | " | N | $n_D^{24.6}$ 1.5450 |
| 114 | CH$_3$ | CH$_3$ | 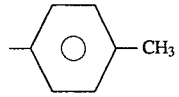 (4-methylphenyl) | S | CH | m.p. 53–57° C. |
| 115 | " | " | " | " | N | m.p. 46–52° C. |
| 116 | C$_2$H$_5$ | " | C$_2$H$_5$ | " | " | $n_D^{24.0}$ 1.5244 |
| 117 | " | " | n-C$_3$H$_7$ | " | " | $n_D^{24.3}$ 1.5210 |
| 118 | " | " | i-C$_3$H$_7$ | " | CH | m.p. 87–90° C. |
| 119 | " | " | " | " | N | $n_D^{23.5}$ 1.5220 |
| 120 | " | " | n-C$_4$H$_9$ | " | " | $n_D^{23.6}$ 1.5190 |
| 121 | " | " | 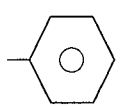 (phenyl) | " | CH | $n_D^{19.8}$ 1.5438 |
| 122 | " | " | " | " | N | m.p. 46–49° C. |
| 123 | n-C$_3$H$_7$ | " | C$_2$H$_7$ | " | CH | m.p. 88–90° C. |
| 124 | " | " | " | " | N | $n_D^{18.5}$ 1.5112 |
| 125 | " | " | i-C$_3$H$_7$ | " | CH | oily product |
| 126 | " | " | " | " | N | oily product |
| 127 | i-C$_3$H$_7$ | " | CH$_3$ | O | CH | m.p. 104–105° C. |
| 128 | " | " | " | S | " | m.p. 112–115° C. |
| 129 | HC≡CCH$_2$— | " | C$_2$H$_5$ | O | " | m.p. 111–112° C. |
| 130 | " | " | " | S | " | m.p. 126–128° C. |
| 131 | HC≡CCH$_2$— | CH$_3$ | C$_2$H$_5$ | S | N | oily product |
| 132 | " | " | n-C$_3$H$_7$ | O | CH | m.p. 111–113° C. |
| 133 | " | " | " | S | N | oily product |
| 134 | FCH$_2$CH$_2$— | " | CH$_3$ | O | CH | m.p. 112–114° C. |
| 135 | " | " | " | S | " | oily product |
| 136 | F$_2$CHCH$_2$— | " | " | O | " | " |
| 137 | " | " | C$_2$H$_5$ | " | " | " |
| 138 | ClCH$_2$CH$_2$— | " | " | " | " | m.p. 92–93° C. |
| 139 | CNCH$_2$CH$_2$— | " | " | " | " | $n_D^{20.6}$ 1.5054 |
| 140 | " | " | n-C$_3$H$_7$ | " | " | oily product |

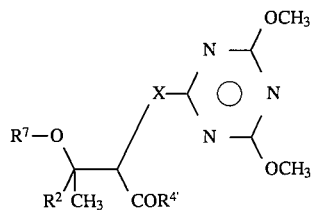

| Compound No. | R$^7$ | R$^2$ | R$^{4'}$ | R$^6$ | X | Physical property |
|---|---|---|---|---|---|---|
| 141 | CH$_3$ | H | OC$_2$H$_5$ | OCH$_3$ | O | |
| 142 | " | " | —OCH$_2$—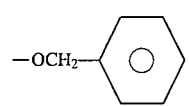 | " | " | |
| 143 | " | " | OH | " | " | |
| 144 | CH$_3$ | H | OH | OCH$_3$ | S | m.p. 111–115° C. |
| 145 | " | CH$_3$ | OC$_2$H$_5$ | " | O | |
| 146 | " | " | —OCH$_2$—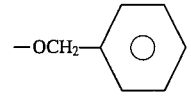 | " | " | |

TABLE 1-continued

| No. | | | | | | |
|---|---|---|---|---|---|---|
| 147 | " | " | OH | " | " | m.p. 94~96° C. |
| 148 | " | " | " | " | S | m.p. 117~118° C. |
| 149 | " | " | " | CH₃ | " | m.p. 121~124° C. |
| 150 | C₂H₅ | H | OC₂H₅ | OCH₃ | O | oily product |
| 151 | " | " | —OCH₂—⟨phenyl⟩ | " | " | m.p. 60~65° C. |
| 152 | " | " | OH | " | " | $n_D^{22.8}$ 1.4790 |
| 153 | " | " | " | " | S | $n_D^{19.6}$ 1.5186 |
| 154 | " | CH₃ / OC₂H₅ | " | | O | $n_D^{22.4}$ 1.4757 |
| 155 | " | " | —OCH₂—⟨phenyl⟩ | " | " | m.p. 83~85° C. |
| 156 | " | " | OH | " | " | $n_D^{22.4}$ 1.4784 |
| 157 | " | " | " | OCH₃ | S | $n_D^{25.6}$ 1.5118 |
| 158 | " | " | " | CH₃ | " | |
| 159 | n-C₃H₇ | " | OC₂H₅ | OCH₃ | O | oily product |
| 160 | " | " | —OCH₂—⟨phenyl⟩ | " | " | $n_D^{20.8}$ 1.5152 |
| 161 | n-C₃H₇ | CH₃ | OH | OCH₃ | O | $n_D^{25.0}$ 1.4873 |
| 162 | " | " | " | " | S | $n_D^{23.1}$ 1.5044 |
| 163 | i-C₃H₇ | H | OC₂H₅ | " | O | |
| 164 | CH₂=CH—CH₂— | " | OH | " | S | |
| 165 | " | CH₃ | OC₂H₅ | " | O | $n_D^{22.3}$ 1.4840 |
| 166 | " | " | —OCH₂—⟨phenyl⟩ | " | " | |
| 167 | " | " | OH | " | S | $n_D^{21.8}$ 1.5354 |
| 168 | HC≡C—CH₂— | H | " | " | " | |
| 169 | " | CH₃ | OC₂H₅ | " | O | $n_D^{23.0}$ 1.4851 |
| 170 | " | " | —OCH₂—⟨phenyl⟩ | " | " | $n_D^{22.8}$ 1.5316 |
| 171 | " | " | OH | " | S | oily product |
| 172 | ClCH₂CH₂— | " | OC₂H₅ | " | O | m.p. 81~83° C. |
| 173 | " | " | —OCH₂—⟨phenyl⟩ | " | " | oily product |
| 174 | " | " | OH | " | " | m.p. 87~88° C. |
| 175 | " | " | " | " | S | m.p. 95~96° C. |
| 176 | BrCH₂CH₂— | " | OC₂H₅ | " | O | oily product |
| 177 | " | " | —OCH₂—⟨phenyl⟩ | " | " | m.p. 73~76° C. |
| 178 | BrCH₂CH₂— | CH₃ | OH | OCH₃ | O | |
| 179 | " | " | " | " | S | |
| 180 | CNCH₂CH₂— | " | " | " | " | m.p. 98~101° C. |

TABLE 1-continued

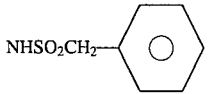

| Compound No. | $R^2$ | $R^3$ | Rhu 5 | $R^{6'}$ | $R^{4''}$ | Physical property |
|---|---|---|---|---|---|---|
| 181 | $CH_3$ | $CH_3$ | $OCH_3$ | $OCH_3$ | $OC_2H_5$ | $n_D^{20.0}$ 1.5230 |
| 182 | " | $C_2H_5$ | " | " | " | $n_D^{20.0}$ 1.4931 |
| 183 | " | $CH_3$ | " | " | $NHSO_2CH_3$ | m.p. 113~114° C. |
| 184 | " | " | " | " | $NHSO_2C_2H_5$ | |
| 185 | " | " | " | " | $NHSO_2C_3H_7$-n | m.p. 117~118° C. |
| 186 | " | " | " | " | $NHSO_2C_3H_7$-i | |
| 187 | " | " | " | " | $NHSO_2C_4H_9$-n | m.p. 102~104° C. |
| 188 | " | " | " | " | $NHSO_2C_4H_9$-sec | |
| 189 | " | " | " | " | $NHSO_2C_4H_9$-i | |
| 190 | " | " | " | " | $NHSO_2C_5H_{11}$-n | m.p. 81~83° C. |
| 191 | $CH_3$ | $CH_3$ | $OCH_3$ | $OCH_3$ | $NHSO_2C_6H_{13}$-n | m.p. 74~75° C. |
| 192 | " | " | " | " | 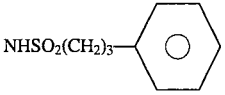 | |
| 193 | " | " | " | " | 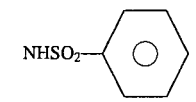 | |
| 194 | " | " | " | " | 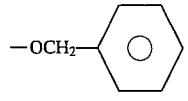 | |
| 195 | " | " | " | " | $NHSO_2CH(CH_3)C_2H_5$ | |

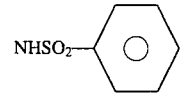

| Compound No. | $R^2$ | $R^3$ | $R^1$ | $R^5$ | $R^6$ | $R^4$ | Physical property |
|---|---|---|---|---|---|---|---|
| 196 | $CH_3$ | $CH_3$ | F | $OCH_3$ | $OCH_3$ | $OC_2H_5$ | $n_D^{20.0}$ 1.5092 |
| 197 | " | " | " | " | " | OH | m.p. 109~110° C. |
| 198 | " | " | " | " | " | $-OCH_2-\bigcirc$ | $n_D^{20.0}$ 1.5326 |
| 199 | " | " | " | " | " | $NHSO_2CH_3$ | m.p. 147° C. |
| 200 | " | " | " | " | " | $NHSO_2C_2H_5$ | m.p. 129~130° C. |
| 201 | " | " | " | " | " | $NHSO_2C_3H_7$-n | m.p. 103° C. |
| 202 | " | " | " | " | " | $NHSO_2C_3H_7$-i | m.p. 118° C. |
| 203 | $CH_3$ | $CH_3$ | F | $OCH_3$ | $OCH_3$ | $NHSO_2C_4H_9$-n | m.p. 98° C. |
| 204 | " | " | " | " | " | $NHSO_2-\bigcirc$ | $n_D^{20.0}$ 1.5602 |
| 205 | $CF_3$ | " | " | " | " | $OC_2H_5$ | $n_D^{20.0}$ 1.4956 |

TABLE 1-continued

| No. | R1 | R2 | R3 | R4 | R5 | R6 | Physical property |
|---|---|---|---|---|---|---|---|
| 206 | 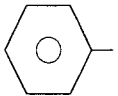 | H | " | " | " | " | $n_D^{20.0}$ 1.5735 |
| 207 | F₃CCH(CH₃)— | " | " | " | " | " | $n_D^{20.0}$ 1.4925 |
| 208 | CH₃ | CH₃ | " | " | " | NHSO₂C₅H₁₁-n | m.p. 105~106° C. |
| 209 | " | " | " | " | " | NHSO₂C₆H₁₃-n | m.p. 78~79° C. |
| 210 | " | " | " | " | " | NHSO₂(CH₂)₃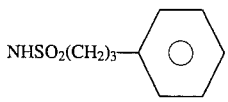 | m.p. 131~134° C. |
| 211 | " | " | " | " | " | NHSO₂CH₂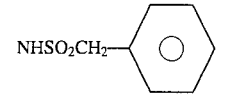 | m.p. 105~106° C. |
| 212 | " | " | " | " | " | NHSO₂CH(CH₃)C₂H₅ | m.p. 101~103° C. |
| 213 | " | " | " | " | " | NHSO₂C₄H₉-i | m.p. 88~90° C. |
| 214 | " | " | " | " | " | NHSO₂CH(CH₃)C₃H₇ | m.p. 102~104° C. |
| 215 | " | " | Cl | " | " | OC₂H₅ | m.p. 47~48° C. |
| 216 | " | " | " | " | " | —OCH₂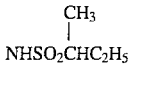 | $n_D^{20.0}$ 1.5570 |
| 217 | " | " | " | " | " | OC₂H₄Si(CH₃)₃ | $n_D^{20.0}$ 1.5131 |
| 218 | C₂H₅ | " | " | " | " | OC₂H₅ | $n_D^{20.0}$ 1.4984 |
| 219 | CH₃ | CH₃ | CN | OCH₃ | OCH₃ | OH | m.p. 104~106° C. |
| 220 | " | " | " | " | " | OCH₃ | m.p. 100~101° C. |
| 221 | " | " | " | " | " | OC₂H₅ | m.p. 65~66° C. |
| 222 | " | " | " | " | " | OC₃H₇-n | m.p. 63~64° C. |
| 223 | " | " | " | " | " | OC₃H₇-i | m.p. 67~68° C. |
| 224 | " | " | " | " | " | OCH₂CH=CH₂ | $n_D^{20.0}$ 1.5268 |
| 225 | " | " | " | " | " | OCH₂C≡CH | $n_D^{20.0}$ 1.5243 |
| 226 | " | " | " | " | " | OC₄H₉-n | $n_D^{20.0}$ 1.5164 |
| 227 | " | " | " | " | " | OC₄H₉-i | |
| 228 | " | " | " | " | " | OC₄H₉-s | |
| 229 | " | " | " | " | " | OC₄H₉-t | m.p. 89~90° C. |
| 230 | " | " | " | " | " | OC₅H₉-cyclo | $n_D^{20.0}$ 1.5206 |
| 231 | " | " | " | " | " | OC₆H₁₁-cyclo | |
| 232 | " | " | " | " | " | O(2-Cl)-C₆H₁₀-cyclo | $n_D^{20.0}$ 1.5178 |
| 233 | " | " | " | " | " | O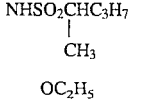 | $n_D^{20.0}$ 1.5457 |
| 234 | " | " | " | " | " | —OCH₂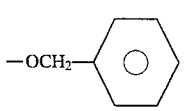 | $n_D^{20.0}$ 1.5367 |
| 235 | " | " | " | " | " | OC₂H₄-Si(CH₃)₃ | m.p. 88~89° C. |
| 236 | " | " | " | " | " | SCH₃ | |
| 237 | CH₃ | CH₃ | CN | OCH₃ | OCH₃ | SC₂H₅ | m.p. 81~83° C. |
| 238 | " | " | " | " | | SC₃H₇-n | |
| 239 | " | " | " | " | " | S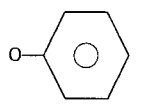 | m.p. 133~135° C. |

TABLE 1-continued

| No. | | | | | | | |
|---|---|---|---|---|---|---|---|
| 240 | " | " | " | " | " | —N(ring with N) | m.p. 122~124° C. |
| 241 | " | " | " | " | " | NHSO$_2$CH$_3$ | m.p. 162~163° C. |
| 242 | " | " | " | " | " | NHSO$_2$C$_2$H$_5$ | m.p. 153~154° C. |
| 243 | " | " | " | " | " | NHSO$_2$—Ph | m.p. 151~153° C. |
| 244 | " | " | " | " | " | OCH$_2$OCH$_3$ | $n_D^{20.0}$ 1.5204 |
| 245 | " | " | " | " | " | OK | m.p. 88~90° C. |
| 246 | " | " | " | " | " | OCH$_2$OC=OC(CH$_3$)$_3$ | $n_D^{20.0}$ 1.5049 |
| 247 | " | " | " | " | " | OCH$_2$CF$_3$ | $n_D^{20.0}$ 1.5001 |
| 248 | " | " | " | " | " | OCH$_2$C$_3$H$_5$-cyclo | m.p. 54~55° C. |
| 249 | " | " | " | " | " | OC$_2$H$_4$OCH$_3$ | $n_D^{20.0}$ 1.5133 |
| 250 | " | " | " | " | " | OC$_2$H$_4$OC$_2$H$_5$ | $n_D^{20.0}$ 1.5100 |
| 251 | " | " | " | " | " | OCH$_2$CH$_2$Cl | $n_D^{20.0}$ 1.5266 |
| 252 | C$_2$H$_5$ | " | " | " | " | OH | $n_D^{20.0}$ 1.5407 |
| 253 | " | " | " | " | " | OCH$_3$ | m.p. 98~99° C. |
| 254 | " | " | " | " | " | OC$_2$H$_5$ | $n_D^{20.0}$ 1.5094 |
| 255 | C$_2$H$_5$ | CH$_3$ | CN | OCH$_3$ | OCH$_3$ | NHSO$_2$CH$_3$ | |
| 256 | " | " | " | " | " | SC$_2$H$_5$ | |
| 257 | " | " | " | " | " | OCH$_2$C≡CH | $n_D^{20.0}$ 1.5270 |
| 258 | " | " | " | " | " | OCH$_2$CH=CH$_2$ | $n_D^{20.0}$ 1.5218 |
| 259 | " | " | " | " | " | OCH$_2$OCOC(CH$_3$)$_3$ | |
| 260 | CH$_3$ | H | " | " | " | OH | |
| 261 | " | " | " | " | " | OCH$_3$ | |
| 262 | " | " | " | " | " | OC$_2$H$_5$ | |
| 263 | " | " | " | " | " | SC$_2$H$_5$ | |
| 264 | " | " | " | " | " | NHSO$_2$CH$_3$ | |
| 265 | C$_2$H$_5$ | CH$_3$ | " | " | " | OCH$_2$CF$_3$ | $n_D^{20.0}$ 1.4912 |
| 266 | " | C$_2$H$_5$ | " | " | " | OC$_2$H$_5$ | m.p. 65~66° C. |
| 267 | C$_3$H$_7$-n | CH$_3$ | " | " | " | " | $n_D^{20.0}$ 1.5084 |
| 268 | C$_2$H$_5$ | " | " | " | " | OCH$_2$OCH$_3$ | $n_D^{20.0}$ 1.5171 |
| 269 | Ph | " | " | " | " | OC$_2$H$_5$ | $n_D^{20.0}$ 1.5531 |
| 270 | H | H | " | " | " | " | $n_D^{20.0}$ 1.5337 |
| 271 | C$_3$H$_7$-i | CH$_3$ | " | " | " | " | $n_D^{20.0}$ 1.3476 |
| 272 | CH$_3$ | " | " | " | " | OCH$_2$CF$_3$ | $n_D^{20.0}$ 1.5001 |
| 273 | " | " | " | " | " | OCH$_2$-cyclopropyl | m.p. 54~55° C. |
| 274 | CH$_3$ | CH$_3$ | CN | OCH$_3$ | OCH$_3$ | OC$_2$H$_4$OC$_2$H$_5$ | $n_D^{20.0}$ 1.5100 |
| 275 | " | " | " | " | " | OC$_2$H$_4$OCH$_3$ | $n_D^{20.0}$ 1.5133 |
| 276 | " | " | " | " | " | OCH$_2$CHF$_2$ | m.p. 99~100° C. |
| 277 | " | " | " | " | " | OCH(CF$_3$)$_2$ | m.p. 77~79° C. |
| 278 | " | " | " | " | " | OCH(CF$_3$)C$_2$F$_5$ | $n_D^{20.0}$ 1.4700 |
| 279 | " | " | " | " | " | OCH$_2$CH$_2$F | m.p. 75~76° C. |
| 280 | " | " | " | " | " | OCH(CH$_2$F)$_2$ | m.p. 77~78° C. |
| 281 | " | " | " | " | " | OCH$_2$CF$_2$CF$_3$ | $n_D^{20.0}$ 1.4742 |
| 282 | " | " | " | " | " | OCH$_2$OC$_2$H$_4$OCH$_3$ | $n_D^{20.0}$ 1.5172 |
| 283 | " | " | " | " | " | OCH$_2$SCH$_3$ | $n_D^{20.0}$ 1.5242 |
| 284 | " | " | " | " | " | OCH$_2$CN | $n_D^{20.0}$ 1.5253 |
| 285 | " | " | " | " | " | OCH$_2$S—Ph | $n_D^{20.0}$ 1.5340 |
| 286 | " | " | " | " | " | ON=C(CH$_3$)$_2$ | $n_D^{20.0}$ 1.5282 |
| 287 | " | " | " | " | " | OCH$_2$OC$_2$H$_5$ | $n_D^{20.0}$ 1.5076 |
| 288 | " | " | " | " | " | OCH$_2$-(pyridyl) | $n_D^{20.0}$ 1.5466 |

TABLE 1-continued

| # | | | | | | R | n |
|---|---|---|---|---|---|---|---|
| 289 | " | " | " | " | " | OCH₂-(2-pyridyl) | $n_D^{20.0}$ 1.5446 |
| 290 | " | " | " | " | " | OCH(CH₃)CH=CH₂ | $n_D^{20.0}$ 1.5176 |
| 291 | " | " | " | " | " | OCH₂C≡CCH₃ | $n_D^{20.0}$ 1.5320 |
| 292 | CH₃ | CH₃ | CN | OCH₃ | OCH₃ | OCH₂CH₂≡CH | $n_D^{20.0}$ 1.5264 |
| 293 | " | " | " | " | " | OCH(CH₃)C≡CH | $n_D^{20.0}$ 1.5247 |
| 294 | " | " | " | " | " | O-(2-CH₃-C₆H₄) | $n_D^{20.0}$ 1.5502 |
| 295 | " | " | " | " | " | O-(3-CH₃-C₆H₄) | $n_D^{20.0}$ 1.5488 |
| 296 | " | " | " | " | " | O-(4-CH₃-C₆H₄) | $n_D^{20.0}$ 1.5492 |
| 297 | " | " | " | " | " | O-(2-Cl-C₆H₄) | $n_D^{20.0}$ 1.4008 |
| 298 | " | " | " | " | " | O-(3-Cl-C₆H₄) | $n_D^{20.0}$ 1.3994 |
| 299 | " | " | " | " | " | O-(4-Cl-C₆H₄) | $n_D^{20.0}$ 1.5524 |
| 300 | " | " | " | " | " | O-(4-CF₃-C₆H₄) | $n_D^{20.0}$ 1.5149 |
| 301 | " | " | " | " | " | O-(3-NO₂-C₆H₄) | $n_D^{20.0}$ 1.5569 |
| 302 | " | " | " | " | " | O-(3-F-C₆H₄) | $n_D^{20.0}$ 1.5382 |

TABLE 1-continued

| 303 | " | " | " | " | " | (Cl,Cl,Cl,Cl-phenoxy structure) | $n_D^{20.0}$ 1.4770 |
| 304 | " | " | " | " | " | (Cl,Cl,Cl-phenoxy structure) | $n_D^{20.0}$ 1.5720 |
| 305 | " | " | " | " | " | OCH(COOC$_2$H$_5$)$_2$ | $n_D^{20.0}$ 1.3534 |
| 306 | CF$_3$ | " | " | " | " | OC$_2$H$_5$ | m.p. 82–84° C. |

Example 2

(1) Preparation of granule 8 parts by weight of Compound 5 was uniformly mixed with 30 parts by weight of bentonite, 59 parts by weight of talc, 1 part by weight of Neopelex powder (trade name, produced by Kao K.K.) and 2 parts by weight of sodium lignosulfonate, and then the mixture was kneaded with addition of a small amount of water, followed by granulation and drying, to obtain a granule.

(2) Preparation of wettable powder 50 parts by weight of Compound 7 was uniformly mixed with 46 parts by weight of kaolin, 2 parts by weight of Neopelex powder (trade name, produced by Kao K.K.) and 2 parts by weight of Demol N (trade name, produced by Kao K.K.), and then the mixture was pulverized to obtain a wettable powder.

(3) Preparation of emulsion 30 parts by weight of Compound 12 was added to 60 parts by weight of xylene, 5 parts by weight of dimethylformamide and 5 parts by weight of Sorpol 3005X (trade name, produced by Toho Kagaku Kogyo) and uniformly mixed to be dissolved therein to obtain an emulsion.

(4) Preparation of dust 5 parts by weight of Compound 24 was uniformly mixed with 50 parts by weight of talc and 45 parts by weight of clay to obtain a dust.

Example 3

(1) Herbicidal test for paddy field

Wagner pots, each having an area of 1/5000 are, were packed with Ube soil (alluvial soil) and planted with seeds or tubers of weeds (barnyardgrass, bulrush and flatstage). Then, the pots were filled with water to a depth of 3 cm.

Each wettable powder of the desired compounds (I) shown in Table 1 prepared in accordance with Example 2 was diluted with water and subjected to dropwise addition treatment by using piper so that an effective concentration of the compound (I) in each herbicide became 20 g/are at 1 leaf stage of barnyardgrass. These plants were controlled in a glass house at an average temperature of 25° C. for 3 weeks, and then herbicidal effects thereof were investigated. As a comparative compound, Compound No. 155 disclosed in Japanese Perovisional Patent Publication No. 85262/1990 represented by the following formula (XIII):

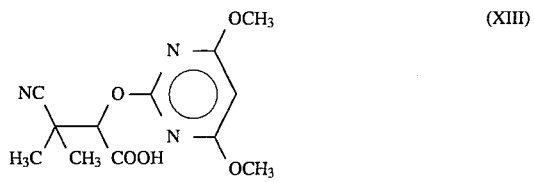

prepared in the same manner as described above was used.

The herbicidal effects were evaluated according to the 6 ranks (0: None (normal development), 1: Less damaged, 2: Slightly damaged, 3: Moderately damaged, 4: Severely damaged and 5: All killed) as compared with non-treated district.

The results are shown in Table 2.

TABLE 2

| Compound | Kind of weed | | |
| --- | --- | --- | --- |
|  | Barnyardgrass | Bulrush | Flatstage |
| 5 | 5 | 5 | 4 |
| 7 | 5 | 5 | 5 |
| 12 | 5 | 5 | 5 |
| 14 | 5 | 5 | 5 |
| 15 | 5 | 5 | 3 |
| 16 | 5 | 5 | 3 |
| 22 | 5 | 5 | 4 |
| 23 | 5 | 5 | 5 |
| 28 | 5 | 5 | 3 |
| 29 | 5 | 5 | 5 |
| 41 | 5 | 5 | 5 |
| 45 | 5 | 5 | 4 |
| 46 | 4 | 3 |  |
| 47 | 5 | 5 | 5 |
| 48 | 5 | 4 |  |
| 49 | 3 | 5 | 4 |
| 50 | 5 | 5 | 5 |
| 51 | 3 | 2 | 2 |
| 53 | 5 | 5 | 4 |
| 55 | 5 | 5 | 4 |
| 57 | 5 | 5 | 4 |
| 63 |  | 5 |  |
| 65 | 5 | 5 | 3 |
| 67 | 5 | 4 |  |
| 68 | 5 | 5 | 5 |
| 69 | 5 | 5 | 4 |
| 70 | 4 | 5 |  |
| 72 | 5 | 5 | 2 |
| 73 | 5 | 5 | 2 |
| 76 | 4 | 5 |  |

TABLE 2-continued

| Compound | Kind of weed | | |
|---|---|---|---|
| | Barnyardgrass | Bulrush | Flatstage |
| 77 | 5 | 5 | 5 |
| 81 | 5 | 5 | 5 |
| 83 | 5 | 5 | 3 |
| 84 | 5 | 5 | 5 |
| 89 | 5 | 5 | 2 |
| 90 | 5 | 5 | 5 |
| 92 | 5 | 5 | 5 |
| 93 | 5 | 5 | 2 |
| 94 | | 3 | |
| 95 | 4 | 4 | |
| 96 | 2 | 4 | |
| 99 | 5 | 5 | 3 |
| 100 | 5 | 5 | 4 |
| 101 | | 5 | 3 |
| 104 | 2 | 5 | 4 |
| 108 | 2 | 4 | 3 |
| 110 | 4 | 5 | 3 |
| 112 | 4 | 5 | 3 |
| 114 | 2 | 5 | 2 |
| 116 | 5 | 5 | 3 |
| 117 | 3 | 5 | 2 |
| 118 | 5 | 5 | 5 |
| 119 | 4 | 5 | 2 |
| 123 | 5 | 5 | 5 |
| 125 | 5 | 5 | 3 |
| 128 | 4 | 5 | 3 |
| 130 | 5 | 5 | 5 |
| 131 | 4 | 5 | 3 |
| 134 | 5 | 5 | 3 |
| 135 | 5 | 5 | 3 |
| 136 | 4 | 5 | 3 |
| 138 | 4 | 5 | 3 |
| 144 | 3 | 3 | 3 |
| 147 | 4 | 5 | 0 |
| 148 | 5 | 5 | 4 |
| 156 | 5 | 5 | 4 |
| 157 | 5 | 5 | 3 |
| 196 | 5 | 5 | 4 |
| 197 | 5 | 5 | 5 |
| 198 | 4 | 3 | |
| 199 | | 5 | 5 |
| 204 | | | |
| 205 | 2 | 5 | |
| 206 | 3 | 5 | 2 |
| 207 | | 5 | |
| 219 | 5 | 5 | 4 |
| 220 | 5 | 5 | 3 |
| 221 | 5 | 5 | 5 |
| 229 | 5 | 5 | |
| 240 | 5 | 5 | 5 |
| 241 | 5 | 5 | 5 |
| 242 | 5 | 5 | 3 |
| 243 | | 5 | |
| 245 | 5 | 5 | 5 |
| 253 | 5 | 5 | 5 |
| 265 | 5 | 5 | 4 |
| 266 | 5 | 5 | |
| 267 | 5 | 5 | |
| 268 | 5 | 5 | 3 |
| 269 | | | |
| 270 | | 5 | |
| 271 | 5 | 4 | 2 |

TABLE 2-continued

| Compound | Kind of weed | | |
|---|---|---|---|
| | Barnyardgrass | Bulrush | Flatstage |
| 272 | 5 | 5 | 5 |
| 273 | 5 | 5 | 3 |
| 274 | 5 | 5 | 2 |
| 275 | 5 | 5 | 3 |
| 276 | 5 | 5 | 4 |
| 277 | 5 | 5 | 4 |
| 278 | 5 | 5 | 4 |
| 279 | 5 | 5 | 4 |
| 280 | 5 | 5 | 5 |
| 281 | 5 | 5 | 4 |
| 282 | 5 | 5 | 5 |
| 283 | 5 | 5 | 2 |
| 284 | 2 | 5 | |
| 285 | 2 | 5 | |
| 286 | 5 | 5 | 3 |
| 287 | 5 | 5 | 5 |
| 288 | 5 | 5 | 4 |
| 289 | 5 | 5 | |
| 290 | 5 | 4 | |
| 291 | 4 | 4 | 2 |
| 292 | 4 | 3 | |
| 293 | 5 | 5 | 4 |
| 294 | 5 | 5 | 4 |
| 295 | 4 | 5 | 3 |
| 296 | 5 | 5 | 3 |
| 297 | 5 | 5 | 5 |
| 298 | 4 | 5 | 2 |
| 299 | 5 | 5 | 4 |
| 300 | 5 | 5 | 3 |
| 301 | 4 | 5 | 2 |
| 302 | 5 | 5 | 4 |
| 303 | 2 | 5 | |
| 304 | 5 | 5 | 3 |
| 305 | 5 | 5 | 4 |
| 306 | 5 | 5 | 5 |
| (XIII) | 3 | 2 | 1 |

(2) Soil treatment test for upland field

Wagner pots, each having an area of 1/5000 are, were packed with Ube soil (alluvial soil), and then each seed of cotton, soy bean, crabgrass, barnyardgrass, foxtail, velvetleaf, common lambsquarter, livid amaranthus, morning glory and cocklebur were planted and covered with soil.

Each wettable powder of the desired compounds (I) shown in Table 1 prepared in accordance with Example 2 was diluted with water and uniformly sprayed on the surface of each soil so that an effective concentration of the compound (I) in each herbicide became 20 g/are. These plants were controlled in a glass house at an average temperature of 25° C. for 3 weeks, and then herbicidal effects thereof were investigated.

The herbicidal effects were evaluated according to the evaluation method described in (1) herbicidal test for paddy field, and the results are shown in Table 3 with the results of Comparative chemical used in (1).

TABLE 3

| Compound | Crop | | Crabgrass | Barnyardgrass | Velvet leaf | Common lambsquarter | Livid amaranthus | Morning glory | Cocklebur |
|---|---|---|---|---|---|---|---|---|---|
| | Cotton | Soy bean | | | | | | | |
| 7 | 1 | | 4 | 4 | 5 | 5 | 5 | 4 | |
| 8 | 0 | | 4 | 5 | 5 | 5 | 4 | 3 | |

TABLE 3-continued

| Compound | Cotton | Soy bean | Crab-grass | Barnyard-grass | Foxtail | Velvetleaf | Livid amaranthus | Morning glory | Cocklebur |
|---|---|---|---|---|---|---|---|---|---|
| 12 | 0 | | 5 | 4 | 5 | 5 | 4 | 4 | |
| 14 | 0 | | 5 | 5 | 5 | 5 | 5 | 4 | |
| 22 | 1 | | 5 | 5 | 4 | 5 | 5 | 4 | |
| 23 | 0 | | 5 | 4 | 4 | 5 | 5 | 3 | |
| 29 | 0 | | 4 | 5 | 3 | 5 | 5 | 4 | |
| 41 | 0 | | 5 | 5 | 5 | 5 | 5 | 4 | 3 |
| 45 | 0 | | 5 | 5 | 3 | 2 | | 3 | 4 |
| 47 | 0 | | 5 | 4 | 5 | 5 | | 4 | 2 |
| 48 | 2 | | 5 | 5 | 5 | 4 | 2 | 4 | 5 |
| 49 | 0 | | 4 | 4 | 5 | 5 | 3 | 4 | 5 |
| 50 | | | 5 | 5 | 5 | 5 | 4 | 5 | 4 |
| 51 | | | 5 | 5 | 5 | 5 | 4 | 5 | 4 |
| 53 | 0 | | 5 | 5 | | 4 | 4 | 4 | |
| 55 | | | 4 | 4 | | 4 | 4 | 5 | |
| 57 | 0 | | 5 | 5 | 5 | 4 | 4 | 4 | 2 |
| 65 | | | 5 | 5 | 5 | 5 | 3 | 5 | 3 |
| 67 | 2 | | 5 | 4 | 2 | 3 | 3 | 4 | 3 |
| 68 | | | 5 | 5 | 5 | 5 | 5 | 4 | 4 |
| 69 | 0 | | 5 | 5 | 5 | 5 | 3 | 4 | 3 |
| 70 | | | 5 | 5 | 5 | 4 | 4 | 5 | 5 |
| 71 | | | 4 | 3 | 5 | 5 | 3 | 5 | 5 |
| 72 | 0 | | 3 | 3 | 5 | 4 | 3 | 5 | 4 |
| 76 | | | 5 | 5 | 3 | 5 | 5 | 3 | 3 |
| 81 | 0 | | 5 | 5 | 5 | 5 | 5 | 3 | 3 |
| 82 | 0 | 2 | 5 | 5 | 5 | 4 | 4 | 4 | 2 |
| 83 | 0 | 0 | 5 | 4 | 3 | 3 | 4 | 4 | 3 |
| 84 | 1 | 1 | 5 | 5 | 4 | 4 | 5 | 4 | 3 |
| 89 | 0 | | 4 | 4 | 4 | 4 | 2 | 4 | 5 |
| 90 | 0 | | 4 | 5 | 4 | 3 | 4 | | |
| 92 | | | 5 | 5 | 3 | 5 | 5 | | 4 |
| 93 | 0 | 0 | 5 | 5 | 5 | 4 | 4 | 5 | 4 |
| 95 | 2 | | 5 | 5 | 5 | 4 | 3 | 3 | 4 |
| 96 | 0 | | 4 | | 2 | 3 | 2 | 5 | |
| 99 | | | 5 | 5 | | 4 | | 5 | 3 |
| 100 | 2 | | 5 | 5 | 5 | 5 | 5 | 4 | |
| 101 | | | 5 | | 2 | 4 | 5 | 4 | 5 |
| 102 | 0 | 0 | | | | 2 | | 2 | 5 |
| 103 | 2 | 2 | | | | | | 4 | 3 |
| 116 | 2 | | 4 | 4 | 5 | 4 | 4 | 4 | |
| 117 | | | 3 | | 4 | 4 | 4 | 4 | 5 |
| 118 | 0 | 0 | 4 | 5 | 3 | 4 | 4 | 5 | |
| 129 | 1 | | 5 | 3 | 3 | 4 | 2 | 4 | 5 |
| 130 | 2 | | 5 | 4 | 5 | 5 | 5 | 4 | 3 |
| 131 | 0 | 1 | 4 | 5 | 4 | | | 4 | 5 |
| 132 | 1 | | 4 | 5 | 4 | 5 | 5 | 5 | 5 |
| 134 | 0 | | 5 | 5 | 5 | 5 | 5 | 5 | |
| 136 | | | 5 | 5 | 4 | 5 | 5 | 4 | 5 |
| 138 | 0 | | 5 | 5 | 4 | 3 | 2 | 4 | 3 |

| Compound | Cotton | Soy bean | Crab-grass | Barnyard-grass | Foxtail | Velvetleaf | Livid amaranthus | Morning glory | Cocklebur |
|---|---|---|---|---|---|---|---|---|---|
| 144 | | | | 4 | 5 | 5 | 5 | | |
| 147 | | | | 5 | 5 | 5 | 5 | | |
| 148 | | | | 5 | 5 | 5 | 5 | | |
| 156 | | | | 5 | 5 | 4 | 5 | | |
| 157 | | | | 5 | 5 | 5 | 5 | | |

| Compound | Cotton | Soy bean | Crab-grass | Barnyard-grass | Velvet leaf | Common lambs-quarter | Livid amaranthus | Morning glory | Cocklebur |
|---|---|---|---|---|---|---|---|---|---|
| 196 | 0 | 1 | | 2 | | 2 | | 2 | 2 |
| 197 | | | 5 | 5 | 5 | 5 | 5 | 2 | |
| 198 | 0 | 0 | | 2 | | 2 | 2 | | |
| 199 | | | | | | | | | |
| 204 | | | | | | | | | |
| 205 | | | | | | | | | |
| 206 | | | | | | | | | |
| 207 | | | | | | | | | |
| 219 | | | | 5 | 5 | 5 | 5 | | |
| 220 | | | | 4 | 5 | 5 | 5 | | |
| 221 | | | | 5 | 5 | 5 | 5 | | |
| 225 | | | | 5 | 5 | 5 | 5 | | |

TABLE 3-continued

| Compound | | | | | | | | | |
|---|---|---|---|---|---|---|---|---|---|
| 229 | 0 | 0 | | | | | | | |
| 234 | | | | 5 | 5 | 5 | 5 | | |
| 240 | | | | 4 | 4 | 4 | 4 | | |
| 241 | | | | 4 | 3 | 4 | 4 | | |
| 242 | 1 | | 4 | 4 | 5 | 4 | 2 | 5 | 4 |
| 243 | 0 | 0 | | | | | | | |
| 244 | 2 | | 5 | 5 | 4 | 5 | 4 | 5 | 4 |
| 245 | | | | 4 | 4 | 5 | 5 | | |
| 246 | | | | 3 | 3 | 4 | 4 | | |
| 253 | 1 | 2 | 5 | 5 | 4 | 4 | 4 | 4 | 5 |
| 265 | 1 | 1 | 2 | | 2 | 4 | 4 | 2 | |
| 266 | 0 | 0 | 2 | | 2 | | | 3 | 2 |
| 267 | 2 | | 4 | 5 | 4 | 5 | 3 | 4 | 5 |
| 268 | 1 | 0 | 2 | 3 | 2 | | 2 | | 3 |
| 269 | 0 | 0 | | 2 | | | | | 2 |
| 270 | 0 | 0 | | | | | | | |
| 271 | 0 | 0 | | | | | | | |
| 272 | 1 | | 5 | 5 | 4 | 3 | 5 | 5 | 4 |
| 273 | 0 | 1 | 5 | 4 | 4 | 2 | | 2 | |
| 274 | 2 | | 5 | 4 | 4 | 2 | 2 | 3 | 2 |
| 275 | 0 | | 5 | 5 | 3 | | 2 | 3 | 3 |
| 276 | 0 | | | | 3 | 2 | | 2 | |
| 277 | 0 | 0 | 5 | 5 | 5 | 4 | 5 | 4 | 4 |
| 278 | 0 | 0 | | | | | | | |
| 279 | 0 | 2 | 5 | 5 | 5 | 4 | 4 | 3 | 4 |
| 280 | 0 | 0 | 3 | 4 | 3 | 2 | | 3 | 2 |
| 281 | 0 | 0 | 4 | 3 | 2 | | | | 2 |
| 282 | 0 | 0 | 3 | | 2 | 3 | 2 | 2 | 3 |
| 283 | 0 | 0 | 2 | | | | 2 | 2 | 3 |
| 284 | 0 | 0 | | | | | 2 | 3 | 2 |
| 285 | | | | | | | | | |
| 286 | 0 | 2 | 3 | | 2 | 4 | 4 | 4 | 3 |
| 287 | 1 | | 2 | 4 | 3 | 4 | 3 | 3 | 2 |
| 288 | 0 | 0 | 2 | 2 | | | 2 | 3 | 2 |
| 289 | 0 | | | 2 | | 2 | | | |
| 290 | 0 | 0 | | | | | | | |
| 291 | 0 | | 2 | 4 | 2 | 2 | 4 | 3 | 3 |
| 292 | 0 | | 2 | 2 | 3 | 3 | 4 | 3 | 2 |
| 293 | 2 | | 4 | 4 | 3 | 5 | 4 | 3 | 2 |
| 294 | 1 | | 5 | 5 | 4 | 4 | 5 | 5 | |
| 295 | 0 | 2 | 3 | 5 | 4 | 4 | 4 | 5 | 3 |
| 296 | 0 | 0 | 4 | 5 | 5 | 5 | 4 | 3 | 3 |
| 297 | 0 | 2 | 5 | 4 | 4 | 4 | 2 | 2 | 3 |
| 298 | 2 | | 5 | 5 | 5 | 4 | 4 | 5 | 3 |
| 299 | 1 | 0 | 2 | | 3 | 3 | 3 | 3 | 2 |
| 300 | 0 | 0 | 2 | | 4 | 4 | 4 | 4 | |
| 301 | 0 | 0 | | | 2 | | | 2 | |
| 302 | 0 | 2 | 4 | 4 | 4 | 3 | 4 | 2 | 2 |
| 303 | 1 | 0 | | | 2 | | | | 3 |
| 304 | 0 | 0 | | | | | 2 | | |
| 305 | 0 | 1 | | | | 2 | | | |
| 306 | 0 | 2 | 2 | 4 | 4 | 5 | 5 | 4 | |
| (XIII) | | | | 3 | 2 | 3 | 3 | | |

(3) Foliar spread test for upland field

Wagner pots, each having an area of 1/5000 are, were packed with volcanic ash soil and then each seed of crabgrass, barnyardgrass, velvetleaf, common lambsquarter, livid amaranthus, morning glory, cocklebur, cotton and soy bean was planted, covered with soil and grown for 2 weeks.

Each wettable powder of the desired compounds (I) shown in Table 1 prepared in accordance with Example 2 was diluted to 2000 ppm with water containing a spreading agent Neoesterin (trade name, produced by Kumiai Kagaku Co.) (500 ppm) and then uniformly sprayed on the above respective plants. After these plants were controlled in a glass house at an average temperature of 25° C. for 3 weeks, the herbicidal effects thereof were investigated.

The herbicidal effects were evaluated according to the evaluation method described in (1) herbicidal test for paddy field, and the results are shown in Table 4 with the results of Comparative chemical used in (1).

TABLE 4

| | Kind of weed | | | | | | |
|---|---|---|---|---|---|---|---|
| Compound | Crabgrass | Barnyardgrass | Velvet leaf | Common lambsquarter | *Livid amaranthus* | Morning glory | Cocklebur |
| 5 | 5 | 5 | 5 | 5 | 5 | 5 | 3 |
| 6 | 5 | 5 | 5 | 5 | 5 | 5 | 3 |
| 7 | 5 | 5 | 5 | 5 | 5 | 5 | 4 |

TABLE 4-continued

| | | | | | | | |
|---|---|---|---|---|---|---|---|
| 12 | 5 | 5 | 5 | 5 | 5 | 5 | |
| 14 | 4 | 5 | 5 | 5 | 5 | 4 | |
| 15 | 5 | 5 | 5 | 5 | 5 | 3 | |
| 16 | 5 | 4 | 5 | 5 | 5 | 5 | |
| 22 | 4 | 5 | 4 | 5 | 5 | 4 | |
| 23 | 4 | 5 | 5 | 5 | 5 | 3 | |
| 28 | 5 | 5 | 5 | 5 | 5 | 5 | |
| 29 | 4 | 5 | 5 | 5 | 5 | 3 | |
| 31 | 5 | 5 | 5 | 5 | 5 | 5 | |
| 41 | 5 | 5 | 5 | 5 | 5 | 5 | 5 |
| 45 | 5 | 5 | 5 | 5 | 5 | 4 | 5 |
| 46 | 4 | 4 | 3 | 4 | 4 | 4 | 5 |
| 47 | 5 | 5 | 5 | 5 | 5 | 5 | 5 |
| 48 | 5 | 5 | 5 | 5 | 5 | 5 | 5 |
| 49 | 4 | 5 | 5 | 5 | 5 | 5 | 5 |
| 50 | 4 | 5 | 5 | 5 | 5 | 5 | 5 |
| 51 | 5 | 5 | 5 | 4 | 3 | 5 | 5 |
| 53 | 4 | 5 | | | | 5 | 5 |
| 55 | 3 | 5 | | 4 | 4 | 5 | 5 |
| 57 | 5 | 5 | 5 | 5 | 5 | 5 | 5 |
| 65 | 3 | 4 | 5 | 2 | | 5 | 5 |
| 67 | 5 | 5 | 5 | 5 | 5 | 5 | 5 |
| 68 | 5 | 5 | 5 | 5 | 5 | 5 | 5 |
| 69 | 5 | 5 | 5 | 5 | 5 | 4 | 5 |
| 70 | 5 | 4 | 5 | 5 | 5 | 5 | 5 |
| 71 | 3 | 3 | 4 | 5 | 5 | 5 | 5 |
| 72 | 4 | 4 | 4 | 5 | 5 | 5 | 5 |
| 73 | 4 | 5 | 5 | 5 | 5 | 5 | 5 |
| 74 | | | 3 | 4 | 4 | 5 | 5 |
| 75 | | | 5 | 3 | 4 | 3 | 5 |
| 76 | 5 | 5 | 5 | 5 | 5 | 5 | 5 |
| 77 | 2 | 2 | 5 | 2 | 2 | 5 | 5 |
| 78 | 2 | 3 | 4 | 4 | 4 | 5 | 5 |
| 81 | 5 | 4 | 5 | 5 | 5 | 5 | 5 |
| 82 | 5 | 4 | 5 | 5 | 5 | 4 | 5 |
| 83 | 4 | 4 | 5 | 5 | 5 | 4 | 5 |
| 84 | 4 | 4 | 5 | 5 | 5 | 5 | 5 |
| 89 | 5 | 5 | 5 | 5 | 5 | 5 | 5 |
| 90 | 5 | 5 | 5 | 5 | 5 | 5 | 5 |
| 92 | 5 | 5 | 5 | 5 | 5 | 5 | 5 |
| 93 | 5 | 5 | 5 | 5 | 5 | 5 | 5 |
| 94 | 3 | 4 | 5 | 4 | 4 | 4 | 5 |
| 95 | 5 | 5 | 4 | 5 | 5 | 5 | 5 |
| 96 | 3 | | 4 | 3 | 3 | 5 | 5 |
| 99 | 3 | 3 | 5 | 3 | 3 | 5 | 5 |
| 100 | 5 | 3 | | 3 | 3 | 5 | 5 |
| 101 | | | | | | 5 | 5 |
| 102 | | | 5 | | 5 | 5 | 5 |
| 103 | | | | | | 5 | 5 |
| 104 | | | 5 | | | 5 | 5 |
| 106 | | | | | | 5 | 5 |
| 108 | | | 4 | | | 4 | 5 |
| 110 | | | 4 | | | 5 | 5 |
| 111 | | | 4 | | | 5 | 5 |
| 112 | | | | | | 5 | 5 |
| 113 | | | | | | 4 | 5 |
| 116 | | | | | | 5 | 5 |
| 117 | 2 | 3 | | | | 5 | 5 |
| 118 | | 3 | | | | 5 | 5 |
| 119 | 4 | 4 | 4 | | | 5 | 5 |
| 120 | | 2 | | 5 | | 5 | 3 |
| 121 | | | | | | 5 | 5 |
| 122 | | | 3 | | | 5 | 5 |
| 123 | | | 5 | | | 5 | 5 |
| 125 | | | 4 | | | 5 | 5 |
| 128 | | | 3 | | | 5 | 5 |
| 129 | 4 | 5 | 5 | 2 | 3 | 5 | 5 |
| 130 | | 4 | | | | 5 | 5 |
| 131 | 5 | 5 | | | 3 | 5 | 5 |
| 132 | | | 5 | | 3 | 5 | 5 |
| 133 | | 2 | 3 | 3 | | 5 | 5 |
| 134 | 5 | 4 | 5 | 3 | 4 | 5 | 5 |
| 135 | 3 | 5 | 5 | | | 5 | 5 |
| 136 | 3 | 3 | 4 | 3 | | 5 | 5 |
| 138 | 3 | 4 | 5 | 5 | 5 | 4 | 5 |
| 139 | 3 | 2 | 5 | | | 5 | 5 |
| 140 | | | 5 | | | 5 | 5 |

Kind of weed

TABLE 4-continued

| Compound | Barnyard-grass | Foxtail | Velvet leaf | Common lambsquarter | Livid amaranthus |
|---|---|---|---|---|---|
| 144 | 5 | 5 | 5 | 5 | 5 |
| 147 | 5 | 5 | 4 | 5 | 5 |
| 148 | 5 | 5 | 5 | 5 | 5 |
| 156 | 5 | 5 | 5 | 5 | 5 |
| 157 | 5 | 5 | 5 | 5 | 5 |
| 160 | 3 | 3 | 5 | 4 | 4 |

| Compound | Crop Cotton | Crop Soy bean | Crab-grass | Barnyard-grass | Velvet-leaf | Common lambsquarter | Livid amaranthus | Morning glory | Cockle-bur |
|---|---|---|---|---|---|---|---|---|---|
| 196 | 0 | | 2 | 5 | 4 | 2 | 4 | 3 | 3 |
| 197 | | | 4 | 5 | 5 | 5 | 5 | 5 | 5 |
| 198 | 1 | | | | 3 | | 2 | 4 | 4 |
| 199 | 1 | | 5 | 5 | 5 | 4 | 4 | 5 | 5 |
| 200 | | | | | | | | | |
| 205 | | | | | | | | | |
| 206 | | | | | | | | | |
| 207 | | | | | | | | | |
| 219 | | | | 5 | 5 | 5 | 5 | | 5 |
| 220 | | | | 5 | 5 | 5 | 5 | | 5 |
| 221 | | | | 5 | 5 | 5 | 5 | | 5 |
| 224 | | | | 5 | 5 | 5 | 5 | | 4 |
| 226 | | | | 5 | 5 | 5 | 5 | | 5 |
| 229 | 2 | 1 | | 2 | | 2 | 2 | 2 | |
| 230 | | | | 4 | 5 | 5 | 5 | | 5 |
| 233 | | | | 4 | 5 | 5 | 5 | | 4 |
| 234 | | | | 4 | 5 | 5 | 5 | | 5 |
| 239 | | | | 4 | 5 | 5 | 5 | | 5 |
| 240 | | | | 5 | 5 | 5 | 5 | | 4 |
| 241 | | | | 4 | 5 | 5 | 5 | | 4 |
| 242 | 1 | | 2 | | 5 | 2 | 3 | 5 | 5 |
| 243 | 0 | | | 2 | 3 | 2 | | 4 | 5 |
| 244 | | | 4 | 5 | 5 | 5 | 5 | 5 | 5 |
| 245 | | | | 5 | 5 | 5 | 5 | | 5 |
| 246 | | | | 5 | 5 | 5 | 5 | | 5 |
| 252 | | | | 3 | 5 | 5 | 5 | | 4 |
| 253 | | | 5 | 5 | 5 | 4 | 4 | 5 | 5 |
| 254 | | | | 5 | 5 | 5 | 5 | | 5 |
| 265 | | | 2 | | 5 | 3 | 2 | 5 | 5 |
| 266 | 1 | 2 | | 2 | 2 | | 2 | | |
| 267 | 0 | 2 | | 2 | | | | | |
| 268 | | | 4 | 4 | 5 | 5 | 5 | 5 | 5 |
| 269 | 0 | 0 | | | 2 | | | | |
| 270 | 0 | 0 | | | | | | | |
| 271 | 1 | 2 | | | | 2 | | 3 | 3 |
| 272 | | | 4 | 5 | 5 | 5 | 5 | 5 | 5 |
| 273 | 2 | | 3 | 5 | 5 | 5 | 5 | 5 | 5 |
| 274 | | | 2 | 4 | 5 | 5 | 5 | 5 | 5 |
| 275 | 1 | | 4 | 5 | 5 | 3 | 2 | 5 | 5 |
| 276 | 2 | | 3 | 5 | 4 | 2 | | 5 | 5 |
| 277 | 0 | | | | 5 | | | 5 | 5 |
| 278 | 0 | | 4 | 4 | 5 | 3 | 3 | 5 | 3 |
| 279 | | | 5 | 5 | 4 | 4 | 4 | 5 | 5 |
| 280 | 2 | | 2 | 2 | 5 | 3 | 3 | 4 | 5 |
| 281 | | | 3 | 4 | 5 | 3 | 2 | 5 | 5 |
| 282 | | | 3 | 5 | 5 | 5 | 5 | 5 | 5 |
| 283 | 2 | | 3 | 4 | 5 | 2 | 3 | 4 | 3 |
| 284 | | | 3 | 2 | 4 | 2 | | 5 | 5 |
| 285 | | | | | | | | | |
| 286 | 2 | | 2 | 3 | 5 | 2 | 3 | 5 | 5 |
| 287 | | | 3 | 3 | 5 | 4 | 4 | 5 | 5 |
| 288 | 2 | | 2 | 4 | 5 | 2 | | 5 | 4 |
| 289 | 0 | | 2 | 5 | 5 | 3 | 3 | 5 | 5 |
| 290 | 0 | 2 | 4 | 5 | 4 | 2 | 3 | 5 | 5 |
| 291 | 2 | | 5 | 4 | 5 | 5 | 5 | 5 | 5 |
| 292 | 2 | | 3 | 5 | 5 | 5 | 5 | 5 | 5 |
| 293 | | | 5 | 5 | 5 | 5 | 5 | 5 | 5 |
| 294 | 0 | | 3 | 5 | 5 | 5 | 3 | 5 | 4 |
| 295 | 2 | | 3 | 5 | 5 | 5 | 5 | 5 | 5 |
| 296 | 2 | | 3 | 4 | 4 | 3 | 5 | 5 | 5 |
| 297 | 2 | | 3 | 5 | 5 | 5 | 5 | 5 | 5 |
| 298 | 1 | | 4 | 5 | 5 | 5 | 5 | 5 | 5 |

TABLE 4-continued

| | | | | | | | | |
|---|---|---|---|---|---|---|---|---|
| 299 | | | 5 | 5 | 5 | 5 | 5 | 5 | 5 |
| 300 | 2 | | 2 | 4 | 4 | 4 | 4 | 5 | 5 |
| 301 | 2 | | 2 | 5 | 5 | 5 | 5 | 5 | 5 |
| 302 | | | 2 | 3 | 5 | 5 | 5 | 5 | 5 |
| 303 | 2 | | 2 | 3 | 4 | 2 | | 4 | 4 |
| 304 | 0 | 2 | | | 2 | 3 | | 4 | 3 |
| 305 | 0 | | 2 | 4 | 4 | 2 | 3 | 5 | 4 |
| 306 | 0 | 2 | | | 2 | | 3 | 5 | 3 |
| (XIII) | | | | 3 | 2 | 3 | 3 | | 2 |

(4) Foliar spread test for upland field at low concentration

Wagner pots, each having an area of 1/5000 are, were packed with volcanic ash soil and then each seed of cotton, crabgrass, barnyardgrass, velvetleaf, common lambsquarter, livid amaranthus and morning glory was planted, covered with soil and grown for 2 weeks.

Each wettable powder of the desired compounds (I) shown in Table 5 prepared in accordance with Example 5 was diluted to 125 ppm with water containing a spreading agent Neoesterin (trade name, produced by Kumiai Kagaku Co.) (500 ppm) and then uniformly sprayed on the above respective plants. After these plants were controlled in a glass house at an average temperature of 25° C. for 3 weeks, the herbicidal effects thereof were investigated.

The herbicidal effects were evaluated according to the evaluation method described in (1) herbicidal test for upland field, and the results are shown in Table 5.

TABLE 5

| | | Kind of weed | | | | | |
|---|---|---|---|---|---|---|---|
| Compound | Cotton | Crab-grass | Barnyard-grass | Velvet leaf | Common lambsquarter | *Livid amaranthus* | Morning glory |
| 3 | 0 | 4 | 5 | 4 | 5 | 5 | 2 |
| 7 | 1 | 5 | 4 | 4 | 5 | 5 | 2 |
| 9 | 1 | 4 | 5 | 5 | 5 | 5 | 5 |
| 19 | 0 | 4 | 4 | 5 | 4 | 4 | 4 |
| 51 | 1 | 4 | 4 | 5 | 5 | 5 | 4 |
| 52 | 0 | 4 | 3 | 5 | 5 | 5 | 4 |

The novel 3-alkoxyalkanoic acid derivative of the present invention has high selectivity to annual and perennial weeds, and also shows excellent herbicidal effect (particularly effective on annual grass weeds and broad-leaved weeds).

We claim:

1. A 3-alkoxybutyrylimidazole compound represented by the formula (Ia):

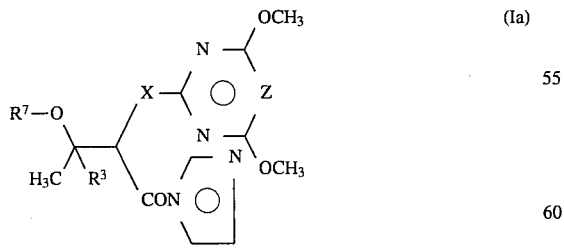

wherein $R^7$ represents a lower alkyl group, a lower alkenyl group, a lower alkynyl group, a halo-lower alkyl group or a cyano-lower alkyl group, $R^3$ represents a hydrogen atom or a lower alkyl group, X represents an oxygen atom or a sulfur atom and Z represents a nitrogen atom.

2. An herbicidal composition, comprising a compound (Ia) according to claim 1 as an active ingredient and a herbicidally effective carrier.

3. A 3-alkoxyalkanoic acid amide compound represented by the formula (Ib):

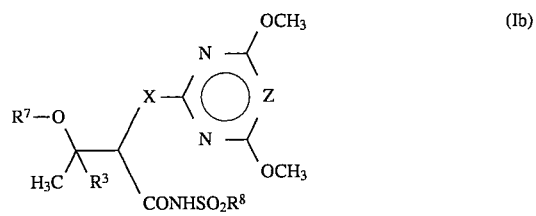

wherein $R^7$ represents a lower alkyl group, a lower alkenyl group, a lower alkynyl group, a halo-lower alkyl group or a cyano-lower alkyl group, $R^3$ represents a hydrogen atom or a lower alkyl group, $R^8$ represents a lower alkyl group, a phenyl group or a phenyl group which is substituted by a straight or branched alkyl group having 1 to 6 carbon atoms or a halogen atom, X-represents an oxygen atom or a sulfur atom and Z represents a nitrogen atom.

4. A compound according to claim 3, wherein $R^7$, $R^3$, and $R^8$ each represent a lower alkyl group.

5. An herbicidal composition, comprising a compound according to claim 4 as an active ingredient and a herbicidally effective carrier.

6. An herbicidal composition, comprising a compound (Ib) according to claim 3 as an active ingredient and a herbicidally effective carrier.

7. A triazine compound represented by the formula (Ic):

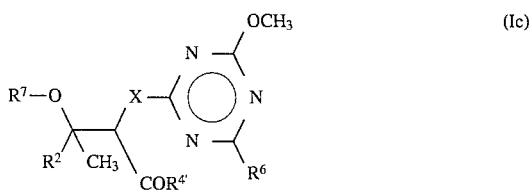

wherein $R^{4'}$ represents a hydroxy group, a lower alkoxy group or a benzyloxy group; $R^2$ represents a hydrogen atom or a lower alkyl group, $R^6$ represents a lower alkoxy group or a lower alkyl group, $R^7$ represents a lower alkyl group, a lower alkenyl group, a lower alkynyl group, a halo-lower alkyl group or a cyano-lower alkyl group and X represents an oxygen atom or a sulfur atom.

8. An herbicidal composition, comprising a compound (Ic) according to claim 7 as an active ingredient and a herbicidally effective carrier.

9. A compound selected from the group consisting of:
2-(4,6-dimethoxy-s-triazin-2-yl)thio-3-methoxy-3-methylbutanoic acid (Compound 148),
ethyl 2-(4,6-dimethoxy-s-triazin-2-yl)oxy-3-ethoxy-3-methylbutanoate (Compound 154),
benzyl 2-(4,6-dimethoxy-s-triazin-2-yl)oxy-3-ethoxy-3-methylbutanoate (Compound 155), and
2-(4,6-dimethoxy-s-triazin-2-yl)oxy-3-ethoxy-3-methylbutanoic acid (Compound 156).

* * * * *